(12) United States Patent
Wang et al.

(10) Patent No.: US 11,338,012 B2
(45) Date of Patent: May 24, 2022

(54) BRAF-BASED POLYPEPTIDES FOR TREATMENT OF CANCER

(71) Applicant: UNIVERSITY OF THE SCIENCES, Philadelphia, PA (US)

(72) Inventors: Zhihong Wang, Philadelphia, PA (US); Zhijun Li, Bala Cynwyd, PA (US); Amber Gunderwala, Havertown, PA (US)

(73) Assignee: University of the Sciences, Philadelphia, PA (US)

( * ) Notice: Subject to any disclaimer, the term of this patent is extended or adjusted under 35 U.S.C. 154(b) by 0 days.

(21) Appl. No.: 15/930,660

(22) Filed: May 13, 2020

(65) Prior Publication Data

US 2020/0360469 A1     Nov. 19, 2020

Related U.S. Application Data

(60) Provisional application No. 62/847,186, filed on May 13, 2019.

(51) Int. Cl.
| | | |
|---|---|---|
| *A61K 38/12* | (2006.01) | |
| *A61P 35/00* | (2006.01) | |
| *A61K 45/06* | (2006.01) | |
| *A61K 31/506* | (2006.01) | |
| *A61K 31/437* | (2006.01) | |

(52) U.S. Cl.
CPC ............. *A61K 38/12* (2013.01); *A61P 35/00* (2018.01); *A61K 31/437* (2013.01); *A61K 31/506* (2013.01); *A61K 45/06* (2013.01)

(58) Field of Classification Search
CPC ................................ A61K 38/12; A61P 35/00
See application file for complete search history.

(56) References Cited

U.S. PATENT DOCUMENTS

2019/0382738 A1* 12/2019 McInnes ................ C12N 9/12

OTHER PUBLICATIONS

Rizzuti et al., 2015, Therapeutic applications of the cell-penetrating HIV-1 Tat peptide, Drug Discovery Today, 20(1): 76-85.*
Parodi et al., 2015, Enabling cytoplasmic delivery and organelle targeting by surface modification of nanocarriers, Nanomedicine, 10(12): 1923-1940.*
Korphaisarn et al., 2016, BRAF-directed Therapy in Metastatic Colorectal Cancer, Cancer J, 22(3): 175-178.*
Beneker, et al., "Design and Synthesis of Type-IV Inhibitors of BRAF Kinase That Block Dimerization and Overcome Paradoxical MEK/ERK Activation", J Med Chem, vol. 62, No. 8, Apr. 25, 2019, pp. 3886-3897.
Cope, et al., "Mechanism of BRAF Activation Through Biochemical Characterization of the Recombinant Full-Length Protein", Chembiochem, vol. 19, No. 18, Sep. 17, 2018, pp. 1988-1997.
Freeman, et al., "Effects of Raf Dimerization and Its Inhibition on Normal and Disease-Associated Raf Signaling", Molecular Cell, vol. 49, Feb. 21, 2013, pp. 751-758.
Gunderwala, et al., "Development of Allosteric BRAF Peptide Inhibitors Targeting the Dimer Interface of BRAF", ACS Chem Biol, vol. 14, No. 7, Jul. 19, 2019, pp. 1471-1480.
Luo, et al., "Identification of BRAF Inhibitors through in silico Screening", J Med Chem, vol. 51, No. 19, Oct. 9, 2008, pp. 6121-6127.
Qin, et al., "Identification of a novel family of BRAFV600E inhibitors", J Med Chem, vol. 55, No. 11, Jun. 14, 2012, pp. 5220-5230.
Rajakulendran, et al., "A dimerization-dependent mechanism drives RAF catalytic activation", Nature, vol. 461, Sep. 24, 2009, pp. S42-S46.
Thevakumaran, et al., "Crystal structure of a BRAF kinase domain monomer explains bassis for allosteric regulation", Nature Structural & Molecular Biology, vol. 22, No. 1, 2014, pp. 37-44.
Wang, et al., "In vitro Enzyme Kinetics Analysis of EGFR", Methods in Molecular Biology, vol. 1487, Humana Press, New York, NY, Abstract Only, Dec. 7, 2016.

* cited by examiner

*Primary Examiner* — Amber D Steele
(74) *Attorney, Agent, or Firm* — Saul Ewing Arnstein & Lehr LLP; Domingos J. Silva; Chihao Wang

(57) ABSTRACT

In one aspect, the invention provides a polypeptide derived from the dimer interface of BRAF, which is useful for treating various types of cancers. In certain embodiments, the polypeptide can be used to treat, prevent, and/or ameliorate a cancer such as but not limited to lung cancer.

22 Claims, 21 Drawing Sheets

Specification includes a Sequence Listing.

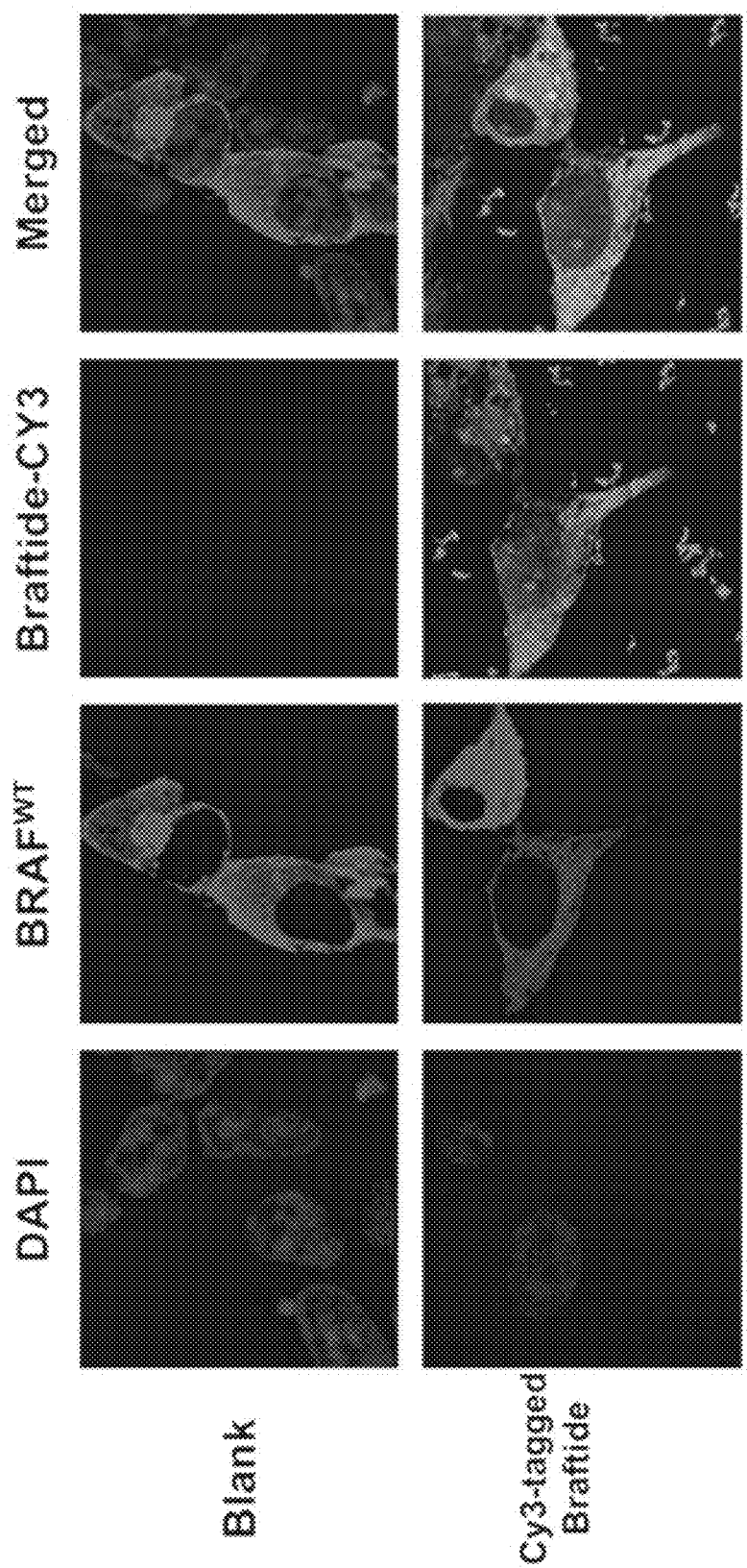

Dimer region sequence alignment for Raf family kinases

BRAF  503 – GVLRKTRHVNILLFMGYS – 520

CRAF  395 – AVLRKTRHVNILLFMGYM – 412

ARAF  356 – QVLRKTRHVNILLFMGFM – 373

BRAF-BASED POLYPEPTIDES FOR TREATMENT OF CANCER

CROSS-REFERENCE TO RELATED APPLICATIONS

The present application claims priority under 35 U.S.C. § 119(e) to U.S. Provisional Application No. 62/847,186, filed May 13, 2019, which application is hereby incorporated by reference in its entirety herein.

STATEMENT REGARDING FEDERALLY SPONSORED RESEARCH OF DEVELOPMENT

This invention was made with government support grant number 1R15GM128099-01 awarded by National Institute of General Medical Sciences (NIGMS)/National Institutes of Health (NIH). The government has certain rights in the invention.

SEQUENCE LISTING

The ASCII text file named "368763-7012US1", created May 12, 2020, comprising 13.1 bytes, is hereby incorporated by reference in its entirety.

BACKGROUND OF THE INVENTION

BRAF, ARAF, and CRAF belong to the family of RAF kinases, which is a core component of the RAS/RAF/MEK/ERK signaling cascade, also known as the mitogen-activated protein kinase (MAPK) cascade. The MAPK cascade mediates signals from cell surface receptors to the nucleus to control vital cellular processes such as cell proliferation and differentiation. Oncogenic mutations in RAS or BRAF induce hyperactivation of MAPK signaling and subsequent tumorigenesis, making this cascade a target of considerable interest for anti-cancer drug development. However, targeting RAS protein has been unsuccessful despite decades of efforts. As the major RAS downstream effector, BRAF is the most successful drug target among the core components of the MAPK cascade. Tumor cells possessing hyperactive MAPK signaling can be sensitized to apoptosis through the selective inhibition of BRAF.

There has been an intense effort to develop inhibitors for BRAF, which has led to two FDA approved inhibitors, dabrafenib (N-{3-[5-(2-aminopyrimidin-4-yl)-2-tert-butyl-1,3-thiazol-4-yl]-2-fluorophenyl}-2,6-difluorobenzene-sulfonamide) and vemurafenib (N-(3-{[5-(4-Chlorophenyl)-1H-pyrrolo[2,3-b]pyridin-3-yl]carbonyl}-2,4-difluorophenyl)propane-1-sulfonamide). These ATP-competitive inhibitors potently inhibit the most common BRAF variant, V600E, which is present in the activation loop of the kinase. Vemurafenib and dabrafenib yield unprecedented response rates in melanoma patients harboring the V600E BRAF mutation. However, they stimulate the same pathway in tumor cells containing wild-type BRAF and oncogenic RAS to induce secondary malignancies, a phenomenon known as 'paradoxical activation'. Moreover, their efficacy is limited only to $BRAF^{V600E}$ tumors, while tumors carrying non-V600 BRAF mutations display intrinsic drug resistance. Non-V600 mutations constitute approximately 50% of BRAF mutations in lung cancer and RAS mutations occur in 30% of cancer patients, suggesting that a substantial number of cancer patients could benefit from alternative therapies targeting BRAF.

These concerns surrounding the current BRAF therapies underscore the urgent need for development of alternative therapeutic strategies to treat cancers. The present invention meets this need.

BRIEF SUMMARY OF THE INVENTION

The invention provides in certain aspects certain polypeptides. The invention provides in other aspects a method of treating cancer in a subject. In certain embodiments, the method comprises administering to the subject a therapeutically effective amount of a polypeptide comprising, consisting essentially of, and/or consisting of certain polypeptides contemplated herein.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 1A illustrates dose-response curves generated from an ELISA for braftide against $FL\text{-}BRAF^{WT/G469A}$. FIG. 1B illustrates computational modeling of braftide binding to the dimer interface of the BRAF kinase domain. FIG. 1C is a dose-response curves for null-braftide against $FL\text{-}BRAF^{WT/G469A}$. Purified $FL\text{-}BRAF^{WT/G469A}$ were incubated with braftide/null-braftide at the indicated concentrations for 90 min and then subjected to an ELISA-based kinase assay with 0.0025 mg $mL^{-1}$ purified, kinase-dead MEK and 40 μM ATP. Error bars represent standard deviations of triplicate measurements. $IC_{50}$ values were obtained from dose-response curve (4-parameter logistic equation) function in Origin, from three independent experiments. FIG. 1D illustrates gel images relating to co-immunoprecipitation of V5-tagged BRAF after pull-down of FLAG tagged BRAF with or without braftide.

FIGS. 2A-2C illustrate TAT-tagged Braftide inhibits $BRAF^{WT/G469A}$ kinase activity in HEK293 cells. HEK293 cells transiently transfected with $BRAF^{WT/G469A}$ were treated with TAT-braftide or TAT peptide at the indicated concentrations (0, 10, 25, 50, 75, and 100 μM) for 4 hrs. Cell lysates were subjected to immunoblotting with the indicated antibodies: anti-BRAF, anti-pMEK, and anti-Actin. FIG. 2A illustrates effect of TAT-braftide on $BRAF^{WT/G469A}$ kinase activity in HEK293 cells. FIG. 2B illustrates effect of TAT control peptide on $BRAF^{WT/G469A}$ kinase activity in HEK293 cells. Western blots are representative of at least three independent experiments. The band intensities from the Western Blots were quantified in ImageJ. FIG. 2C illustrates confocal microscopy images of HEK293 cells treated with 25 μM braftide-Cy3 for 2 hr and stained with FLAG antibody for BRAF.

FIG. 3A illustrates proteasome inhibition with Bortezomib prior to TAT-braftide treatment rescued BRAF levels but not pMEK levels. HEK293 cells transiently transfected with $BRAF^{WT}$ were pre-treated with 0.4 μM of Bortezomib for 5 hr, followed by TAT-braftide treatment at the indicated concentrations (0, 75, and 100 μM) for 4 hr. FIG. 3B illustrates quantification of BRAF protein levels after rescue with Bortezomib. FIG. 3C illustrates half-life of $BRAF^{WT}$ with cycloheximide (CHX) treatment in the presence or absence of TAT-braftide. HEK293 cells transiently transfected with BRAFWT were treated with 200 μg mL-1 of cycloheximide alone or in combination with 75 μM of braftide for the indicated time points (0, 2, 4, 6, 8, and 10 hr). FIG. 3D illustrates quantification of the Western Blot to determine the half-life ($t_{1/2}$) of BRAF. Western blots are representative of at least three independent experiments.

FIG. 4A illustrates sequence alignment of the dimer interface of three RAF family members, ARAF, BRAF, and CRAF (SEQ ID NO:49, BRAF; SEQ ID NO:50, CRAF; SEQ ID NO:51, ARAF). FIG. 4B illustrates HEK293 cells transiently transfected with two plasmid constructs encoding Flag-BRAF and MBP-CRAF at three molar ratios, 1:1, 1:2, and 1:3. The cells were treated with 100 μM of TAT-braftide for 4 hr. FIG. 4C illustrates HEK293 cells transfected with p61-$BRAF^{V600E}$ and treated with TAT-braftide at the indicated concentrations for 4 hr. Western blots are representative of at least three independent experiments.

FIG. 5A illustrates dose-response curves for braftide/dabrafenib combination treatment and dabrafenib alone against FL-$BRAF^{WT}$. FIG. 5B illustrates $IC_{50}$ curves for braftide/dabrafenib combination treatment and dabrafenib alone against FL-$BRAF^{G469A}$. $BRAF^{WT/G469A}$ were pre-treated with braftide at concentrations lower than the $IC_{50}$ (WT:70 nM; G469A: 10 nM) and then treated with dabrafenib at the indicated concentrations. $IC_{50}$ values were obtained from a dose-response curve (4-parameter logistic equation) in Origin, from three independent experiments. FIGS. 5C-5D illustrate effects of combination treatment of TAT-braftide and dabrafenib in HEK293 cells overexpressing $BRAF^{WT}$ or $BRAF^{G469A}$, respectively. Cells were pre-treated with braftide (75 μM) for 2 hr and then dabrafenib was added at the indicated concentrations (0. 0.1, 0.5, 1, 5, and 10 μM) for 1 hr. Western blots are representative of at least three independent experiments.

FIG. 6A illustrates that the HCT116 cells were treated with braftide at the indicated concentrations (0, 1, 10, 25, 50, and 75 μM) for 4 hr. Western blots are representative of at least three independent experiments. HCT116 (FIG. 6B) and HCT-15 (FIG. 6C) cells were treated with braftide or TAT control peptide at the indicated concentrations for 48 hr. Cell viability was determined through the WST assay according to manufacturer's instructions. $IC_{50}$ values were obtained from a dose-response curve (4-parameter logistic equation) in Origin, from three independent experiments.

DETAILED DESCRIPTION OF THE INVENTION

Figure 1A:
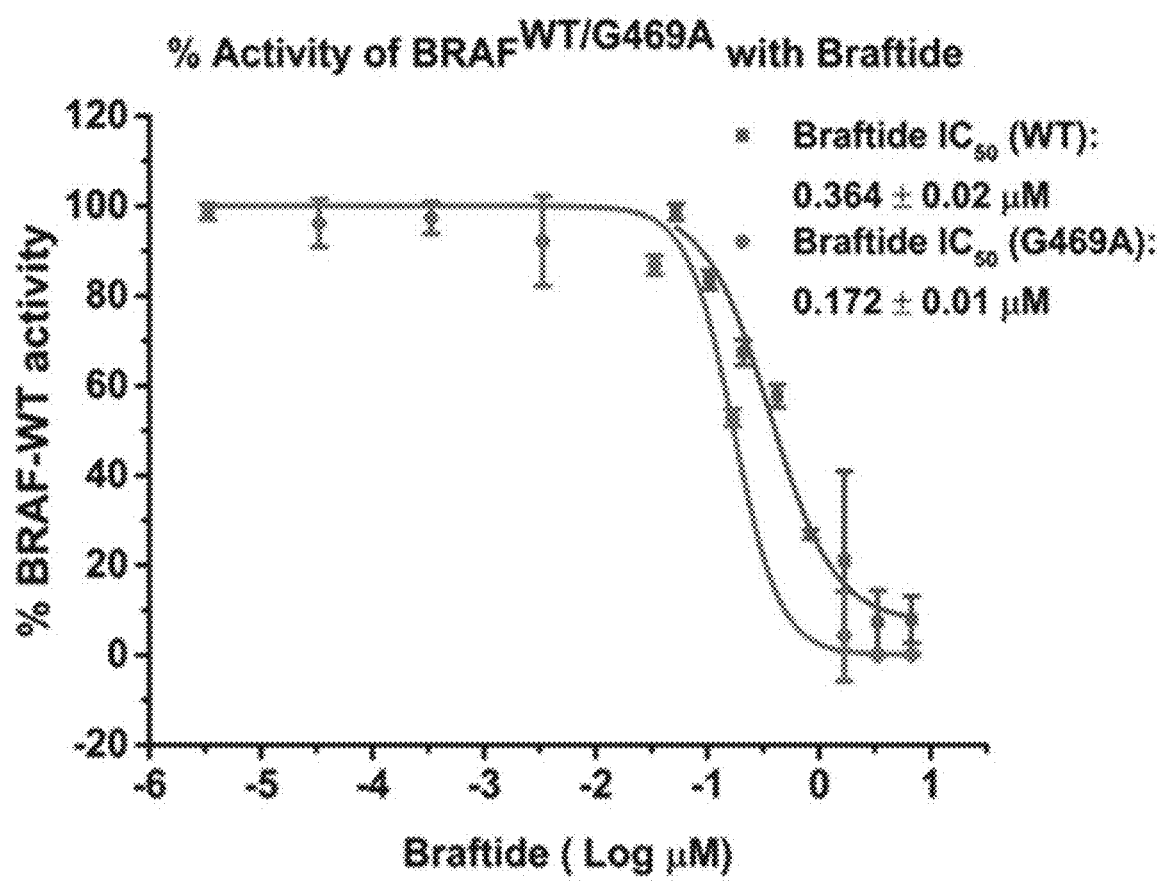
FIGS. 1A-1D illustrate that braftide inhibits BRAF kinase activity by disrupting BRAF dimers.

Unlike $BRAF^{V600E}$, which functions as a monomer, both wild-type BRAF and non-V600 BRAF mutants require an intact dimer interface (DIF) to be functional. BRAF DIF is present in the kinase domain of BRAF at the tail end of the α-C helix. It spans about 20 residues (aa 501-520), with R509 being the central residue that is critical for dimer integrity. RAF dimerization is stabilized by mostly a hydrogen bond network involving R509, L515, and M517. The triple mutation R509/L515/M517 completely abolishes the kinase activity of wild-type BRAF. Furthermore, side effects of current BRAF inhibitors, including drug resistance and paradoxical activation, are contingent on the same DIF. Many of the ATP-competitive inhibitors promote RAF dimerization in a RAS-dependent manner.

As shown herein, allosteric inhibitors capable of disrupting the DIF of BRAF can abrogate hyperactivated MAPK signaling driven by non-V600 BRAF mutations or RAS mutations, while overcoming the major limitations of current BRAF inhibitors. This DIF region is conserved across the RAF family members, but not in other protein kinases, therefore inhibitors of the invention can achieve higher specificity towards RAF, in comparison with ATP-competitive inhibitors.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, oncology, and peptide chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "cancer" is defined as disease characterized by the rapid and uncontrolled growth of aberrant cells. Cancer cells can spread locally or through the bloodstream and lymphatic system to other parts of the body. Examples of various cancers include but are not limited to, bone cancer, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. A tumor may be benign (benign tumor) or malignant (malignant tumor or cancer). Malignant tumors can be broadly classified into three major types. Malignant tumors arising from epithelial structures are called carcinomas, malignant tumors that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other tumors include, but are not limited to neurofibromatosis.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount" or "therapeutically effective amount" or "pharmaceutically effective amount" of a compound are used interchangeably to refer to the amount of the compound that is sufficient to provide a beneficial effect to the subject to which the compound is administered.

As used herein, an "instructional material" includes a publication, a recording, a diagram, or any other medium of expression, which can be used to communicate the usefulness of the compound and/or composition of the invention in the kit for treating or preventing diseases or disorders recited herein. Optionally, or alternately, the instructional material may describe one or more methods of treating or preventing diseases or disorders in a cell or a tissue of a mammal. The instructional material of the kit of the invention may, for example, be affixed to a container, which contains the chemical compound and/or composition of the invention or be shipped together with a container, which contains the chemical composition and/or composition. Alternatively, the instructional material may be shipped separately from the container with the intention that the instructional material and the compound be used cooperatively by the recipient.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound include, but are not limited to, intravenous, oral, aerosol, parenteral, ophthalmic, pulmonary and topical administration.

A "prophylactic" treatment is a treatment administered to a subject who does not exhibit signs of a disease or exhibits only early signs of the disease for the purpose of decreasing the risk of developing pathology associated with the disease.

The phrase "reduction of growth," as used herein, refers to any reduced growth, replication rate, or colony formation exhibited by a neoplastic cell, a cancer cell, or a tumor in response to some therapeutic agent, treatment, or clinical intervention, such as radiation. For example, a neoplastic cell may exhibit a reduction in the cell's growth rate or its ability to replicate and form colonies in vitro or in vivo (e.g., when implanted as a tumor in an animal) in response to radiation.

The phrase "reduction in viability," as used herein, refers to any reduction in survival exhibited by a neoplastic cell, a cancer cell, or a tumor in response to some chemotherapeutic agent, treatment, or clinical intervention, such as radiation. A neoplastic cell, a cancer cell, or a tumor may exhibit reduced viability in response to any such intervention by inhibition of progression of the cell through the cell cycle; damaged nucleic acids, proteins, or other macromolecules in a cell, induced terminal differentiation (senescence), in which the cell no longer replicates; inhibited cellular repair of nucleic acids; or increased rates of cell death by inducing apoptosis or "mitotic catastrophe"—a form of necrosis, when DNA damage levels are beyond those that can be effectively repaired.

A "therapeutic" treatment is a treatment administered to a subject who exhibits signs of pathology for the purpose of diminishing or eliminating those signs.

"Treating," as used herein, means reducing the frequency with which symptoms are experienced by a patient or subject, or administering an agent or compound to reduce the severity with which symptoms are experienced by a patient or subject. An appropriate therapeutic amount in any individual case may be determined by one of ordinary skill in the art using routine experimentation.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

In one aspect, the invention provides a polypeptide for treating various types of cancers. In certain embodiments, the polypeptide can be used to treat, prevent, and/or ameliorate a cancer such as but not limited to lung cancer, colon cancer, melanoma, and/or associated secondary malignancies of melanoma.

In certain embodiments, the polypeptide (braftide) comprises, consisting essentially of, and/or consists of a 10-mer having sequence TRHVNILLFM (SEQ ID NO:1), which is derived from the dimer interface of BRAF.

In certain embodiments, the polypeptide comprises, consisting essentially of, and/or consists the amino acid sequence of SEQ ID NO:8.

In certain embodiments, the polypeptide comprises, consisting essentially of, and/or consists the amino acid sequence of SEQ ID NO:9.

In certain embodiments, at least one amino acid within the polypeptide, and/or at carboxy-terminus, and/or at the amino-terminus is methylated, amidated, acetylated, and/or substituted with any other chemical group without adversely affecting activity of the polypeptide within the methods of the invention.

In certain embodiments, the polypeptide is cyclized. In certain embodiments, the N- and the C-termini of the polypeptide are directly covalently linked through an amide bond so as to form a cyclic peptide. In certain embodiments, the N- and the C-termini of the polypeptide are covalently linked through a peptide linker so as to form a cyclic peptide. In certain embodiments, the polypeptide comprises two cysteine residues (which, for example, may be present at the C-terminus and/or N-terminus and/or a non-terminal residue and/or a linker conjugated to the C-terminus and/or a linker conjugated to the N-terminus), which can react to form a cystine residue and cyclize the polypeptide. In certain embodiments, the peptide linker comprises 1, 2, 3, 4, 5, or more than 5 amino acids.

In certain embodiments, the polypeptide is a fusion polypeptide, for example, wherein the polypeptide of the invention is fused to a cell penetrating peptide.

In certain embodiments, the cell penetrating peptide is an amphipathic peptide. In other embodiments, the cell penetrating peptide is a cationic peptide.

In certain embodiment, the cell penetrating peptide comprises sequence GRKKRRQRRRPQ (SEQ ID NO:2).

In certain embodiments, the cell penetrating peptide is at least one of the following (wherein lower case indicates D-stereochemistry):

Antennapedia (43-58)
SEQ ID NO: 10
RQIKIWFQNRRMKWKK

BAC715-24
SEQ ID NO: 11
PRPLPFPRPG

BMV Gag-(7-25)
SEQ ID NO: 12
KMTRAQRRAAARRNRWTAR

BUFORIN II
SEQ ID NO: 13
TRSSRAGLQFPVGRVHRLLRK

CADY
SEQ ID NO: 14
GLWRALWRLLRSLWRLLWRA

CCMV Gag-(7-25)
SEQ ID NO: 15
KLRTRAQRRAAARKNKRNTR

Cell Penetrating ARF Peptide (26-44)
SEQ ID NO: 16
H-D-Arg-D-Arg-D-Arg-D-Arg-D-Arg-D-Arg-D-Arg-D-Arg- D-Arg-Lys-Phe-Val-Arg-Arg-Ser-Arg-Arg-Pro-Arg-Thr- Ala-Ser-Cys-Ala-Leu-Ala-Phe-Val-Asn-OH D-TAT
SEQ ID NO: 17
rrrqrrkkr

FHV COAT-(35-49)
SEQ ID NO: 18
RRRRNRTRRNRRRVR hCT (9-32)
SEQ ID NO: 19
LGTYTQDFNKFHTFPQTAIGVGAP

HIV-1 Rev (34-50)
SEQ ID NO: 20
TRQARRNRRRWRERQR

HN-1
SEQ ID NO: 21
TSPLNIHNGQKL

HTLV-II Rex-(4-16)
SEQ ID NO: 22
TRRQRTRRARRNR

K-FGF
SEQ ID NO: 23
AAVALLPAVLLALLAP

Ku70
SEQ ID NO: 24
VPMLKPMLKE

MAP

-continued

KLALKLALHALKAALKLAKLALKLALKALKAALKLA    SEQ ID NO: 25

MPG (Pa)

GALFLAFLAAALSLMGLWSQPKKKRRV    SEQ ID NO: 26

MPG (Pb)

GALFLGFLGAAGSTMGAWSQPKKKRKV    SEQ ID NO: 27

P22 N-(14-30)

NAKTRRHERRRKLAIER    SEQ ID NO: 28

Pen2W2F

RQIKIFFQNRRMKFKK    SEQ ID NO: 29

Pep-1

KETWWETWWTEWSQPKKKRRV    SEQ ID NO: 30

Pep-7

SDLWEMMMVSLACQY    SEQ ID NO: 31 plsl-1

RVIRVWFQNKRCKDKK    SEQ ID NO: 32 pVEC

LLIILRRRIRKQAHAHSK    SEQ ID NO: 33

R7W

RRRRRRRW    SEQ ID NO: 34

RVG-9R

YTIWMPENPRPGTPCDIFTNSRGKRASNGGGGRRRRRRRRR    SEQ ID NO: 35

SAP

VRLPPPVRLPPPVRLPPP    SEQ ID NO: 36

SV-40 Large T-antigen Nuclear Localization Signal

CGGGPKKKRKVED    SEQ ID NO: 37

SynB (1)

RGGRLSYSRRRFSTSTGR    SEQ ID NO: 38

TAT (HIV-1 peptide)

YGRKKRRQRRR    SEQ ID NO: 39

TAT (HIV-1 (48-61))

GRKKRRQRRRPPQQ    SEQ ID NO: 40

TAT (HIV-1 (49-57))

RKKRRQRRR    SEQ ID NO: 41

TAT Derivative: R9-Tat

GRRRRRRRRRPPQ    SEQ ID NO: 42

TAT P59W

GRKKRRQRRRPWQ    SEQ ID NO: 43

Transportan

GWTLNSAGYLLGKINLKALAALAKKIL    SEQ ID NO: 44

VP-22

DAATATRGRSAASRPTERPRAPARSASRPRRPVD    SEQ ID NO: 45 p-Antp

RQIKIWFQNRRMKWKK    SEQ ID NO: 46

$Arg_9$ $R_9$    SEQ ID NO: 47 or functionally equivalent variants thereof.

In certain embodiments, the cell penetrating peptide is fused to the polypeptide via a linker.

In certain embodiments, the linker comprises polyethylene glycol chains (PEGs), peptides, and/or peptide nucleic acids (PNAs).

In certain embodiments, the linker is covalently linked to the N-terminus of the polypeptide. In other embodiments, the C-terminus of the linker is not GVLRK (SEQ ID NO:3). In yet other embodiments, the C-terminus of the linker is not VLRK (SEQ ID NO:4). In yet other embodiments, the C-terminus of the linker is not LRK (SEQ ID NO:5). In yet other embodiments, the C-terminus of the linker is not RK. In yet other embodiments, the C-terminus of the linker is not K.

In certain embodiments, the linker is covalently linked to the C-terminus of the polypeptide. In other embodiments, the N-terminus of the linker is not GYST (SEQ ID NO:6). In yet other embodiments, the N-terminus of the linker is not GYS (SEQ ID NO:7). In yet other embodiments, the N-terminus of the linker is not GY. In yet other embodiments, the N-terminus of the linker is not G.

In certain embodiments, the cell penetrating peptide is covalently linked to the N-terminus of the polypeptide. In other embodiments, the C-terminus of the cell penetrating peptide is not GVLRK (SEQ ID NO:3). In yet other embodiments, the C-terminus of the cell penetrating peptide is not VLRK (SEQ ID NO:4). In yet other embodiments, the C-terminus of the cell penetrating peptide is not LRK (SEQ ID NO:5). In yet other embodiments, the C-terminus of the cell penetrating peptide is not RK. In yet other embodiments, the C-terminus of the cell penetrating peptide is not K.

In certain embodiments, the cell penetrating peptide is covalently linked to the C-terminus of the polypeptide. In other embodiments, the N-terminus of the cell penetrating peptide is not GYST (SEQ ID NO:6). In yet other embodiments, the N-terminus of the cell penetrating peptide is not GYS (SEQ ID NO:7). In yet other embodiments, the N-terminus of the cell penetrating peptide is not GY. In yet other embodiments, the N-terminus of the cell penetrating peptide is not G.

In certain embodiments, the peptide linker comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids.

In certain embodiments, the linker comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 ethylene glycol ($-CH_2CH_2O-$ or $-OCH_2CH_2-$) units.

In another aspect, the invention provides a pharmaceutical composition comprising the polypeptide of the invention.

Methods

In another aspect, the invention provides a method for treating cancer in a subject in need thereof. In certain embodiments, the method comprises administering to the subject a therapeutically effective amount of the polypeptide of the invention. In certain embodiments, the cancer comprises oncogenic RAS mutation(s) and/or BRAF mutation(s). In certain embodiments, the cancer includes lung cancer, colon cancer, melanoma, and/or associated secondary malignancies of melanoma.

In certain embodiments, the polypeptide of the invention is as described elsewhere herein. In certain embodiments, the polypeptide inhibits BRAF kinase activity.

Oncogenic BRAF mutants require an intact dimer interface (DIF) to be functional. Therefore, allosteric inhibitors capable of disrupting the DIF of BRAF can abrogate hyperactivated MAPK signaling. In certain embodiments, the polypeptide blocks formation of BRAF dimer. In certain embodiments, the BRAF dimer is a BRAF homodimer. In certain embodiments, the BRAF dimer is BRAF/CRAF heterodimer. In certain embodiments, the BRAF dimer comprises $BRAF^{V600E}$ mutation. In certain embodiments, the BRAF dimer does not comprise $BRAF^{V600E}$ mutation. In certain embodiments, the BRAF dimer comprises $BRAF^{non-V600E}$ mutations.

In certain embodiments, the administering causes proteolysis of BRAF. In certain embodiments, administering causes proteolysis of MEK.

In certain embodiments, the polypeptide inhibits BRAF with the $IC_{50}$ value of about 120 nM to about 400 nM. In certain embodiments, the BRAF comprises oncogenic $BRAF^{G469A}$ mutation.

In certain embodiments, the administering causes apoptosis in cancer cells. In certain embodiment, the tumor cells possessing hyperactive MAPK signaling can be sensitized to apoptosis through selective inhibition of BRAF. In certain embodiments, the administering does not cause any, or causes insignificant, apoptosis in non-cancerous cells.

In certain embodiments, the polypeptide is administered as part of a pharmaceutical composition. In certain embodiments, the subject is not administered any additional chemotherapeutic agent or anti-cell proliferation agent.

In certain embodiments, the subject is not administered any additional chemotherapeutic agent or anti-cell proliferation agent in an amount sufficient to treat or prevent the cancer in the subject.

In certain embodiments, the method further comprises administering to the subject at least one additional agent selected from radiation, a chemotherapeutic agent, an anti-cell proliferation agent, a gene therapy agent, and an immunotherapy agent. In certain embodiments, the polypeptide and at least one additional compound are co-administered to the subject. In certain embodiments, the polypeptide and at least one additional compound are co-formulated. In certain embodiments, at least one additional compound is an ATP-competitive BRAF inhibitor. In certain embodiments, the ATP-competitive BRAF inhibitors comprises dabrafenib or vemurafenib.

ATP-competitive inhibitors such as vemurafenib and dabrafenib potently inhibit the most common BRAF variant, V600E, which is present in the activation loop of the kinase. However, these drugs also stimulate the same pathway in tumor cells containing wild-type BRAF and oncogenic RAS to induce secondary malignancies, a phenomenon known as 'paradoxical activation'. In certain embodiments, the polypeptide of the invention does not induce paradoxical activation. Advantageously, in certain embodiment, the combination of ATP competitive inhibitors and the polypeptide of the invention eliminates paradoxical activation.

In certain embodiments, the subject is a mammal. In certain embodiments, the subject is a human.

Kit

In yet another aspect, the invention provides a kit comprising a composition comprising at least one polypeptide of the invention, and an instructional material for use thereof, wherein the instructional material comprises instructions for treating cancer in a subject in need thereof. In certain embodiments, the composition is as described elsewhere herein. In certain embodiments, the polypeptide is as described elsewhere herein.

Combination Therapies

In certain embodiments, the compounds of the present invention are useful in the methods of present invention in combination with one or more additional compounds useful for treating the diseases or disorders contemplated within the invention. These additional compounds may comprise compounds of the present invention or compounds, e.g., commercially available compounds, known to treat, prevent, or reduce the symptoms of the diseases or disorders contemplated within the invention.

Non-limiting examples of additional compounds contemplated within the invention include chemotherapeutic agents, anti-cell proliferation agents, gene therapy agents, immunotherapy agents, and radiation. In certain embodiments, the method of the invention can be used in combination with one or more compounds selected from, but not necessarily limited to, the group consisting of taxotere, cyclophosphamide, paclitaxel, fluorouracil, doxorubicin, cycloheximide, olaparib.and temozolomide. In other embodiments, the method of the invention can be used in combination with any chemotherapeutic, gene therapy or immunotherapy compound or treatment regimen known in the art. In yet other embodiments, the method of the invention can be used in combination with chemotherapeutic compounds known to treat cancer and/or radiation therapy.

The compounds of the present invention may be administered before, during, after, or throughout administration of any therapeutic agents used in the treatment of a subject's disease or disorder.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions useful within the present invention to a patient, preferably a mammal, more preferably a human, may be carried out using known procedures, at dosages and for periods of time effective to treat a disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the present invention is from about 1 and 5,000 mg/kg of body weight/per day. One of ordinary skill in the art is able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health, and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the present invention employed in the pharmaceutical composition at levels lower than that required in order to achieve the desired therapeutic effect and gradually increase the dosage until the desired effect is achieved.

In particular embodiments, it is advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the present invention are dictated by and directly dependent on the unique characteristics of the therapeutic compound and the particular therapeutic effect to be achieved, and the limitations inherent in the art of compounding/formulating such a therapeutic compound for the treatment of a disease or disorder in a patient.

In certain embodiments, the compositions useful within the invention are formulated using one or more pharmaceutically acceptable excipients or carriers. In certain embodiments, the pharmaceutical compositions of the present invention comprise a therapeutically effective amount of a compound useful within the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions useful within the invention are administered to the patient in dosages that range from one to five times per day or more. In other embodiments, the compositions useful within the invention are administered to the patient in range of dosages that include, but are not limited to, once every day, every two days, every three days to once a week, and once every two weeks. It is readily apparent to one skilled in the art that the frequency of administration of the various combination compositions useful within the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physician taking all other factors about the patient into account.

Compounds for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between.

In some embodiments, the dose of a compound is from about 1 mg and about 2,500 mg. In some embodiments, a dose of a compound of the present invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating a disease or disorder) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the present invention, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like. They may also be combined where desired with other active agents, e.g., other anti-tumor agents.

The term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Routes of administration of any of the compositions of the present invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral administration, particularly suitable are tablets, dragees, liquids, drops, or capsules, caplets and gelcaps. The compositions intended for oral use may be prepared according to any method known in the art and such compositions may contain one or more agents selected from the group consisting of inert, non-toxic pharmaceutically acceptable excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulfate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration

For parenteral administration, the compounds may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the present invention may be administered in the form of microparticles, for example, by injection or in the form of wafers or discs by implantation.

In certain embodiments, the compounds of the present invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound depends on the age, sex and weight of the patient, the current medical condition of the patient and the progression of the disease or disorder in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the present invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, with art-recognized alternatives and using no more than routine experimentation, are within the scope of the present application.

It should be understood that the method and compositions that would be useful in the present invention are not limited to the particular formulations set forth in the examples. The following examples are put forth so as to provide those of ordinary skill in the art with a complete disclosure and description of how to make and use the composition and therapeutic methods of the invention, and are not intended to limit the scope of what the inventor regard as his invention. The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Materials and Methods

Peptides:

Peptides were purchased from Lifetein with TFA removal. Purity was determined through HPLC (>95%) and confirmed through mass spectrometry.

Plasmids:

6×-HIS-BRAF-WT/FLAG was prepared as previously described (Cope, et al., 2018, *Chembiochem: A European Journal of Chemical Biology* 19, 1988-1997). 6×-HIS/BRAF$^{G469A}$/FLAG and MBP-CRAF-FLAG were created using common cloning procedures with pcDNATM 4/TO (Invitrogen) as the vector. 6×-HIS-BRAF-V600E/FLAG and 6×-HIS-BRAFp61-V600E/FLAG were prepared similarly.

Co-Immunoprecipitation of BRAF Homodimers with Braftide Treatment:

V5-tagged BRAF$^{WT}$ and FLAG-tagged BRAFWT were co-transfected in HEK293 cells for 48 hrs. Cells were harvested after this time and lysed in modified RIPA buffer (50 mM HEPES pH 7.4, 150 mM NaCl, 0.1% NP40 (IGEPAL630), 1 mM EDTA, 5% glycerol, 1 mM PMSF, 20 mM BGP, 2.5 mM sodium pyrophosphate, and 1 protease inhibitor tablet) and incubated with rotation for ~2 hrs at 4° C. Cell lysate (0.5 mg) was then treated with braftide (50 µM) for 90 min with rotation and then bound to FLAG-M2 magnetic resin. After few wash steps, the resin was resuspended in dilution buffer and analyzed through immunoblotting for co-immunoprecipitation FLAG and V5-tagged BRAF.

Cell Viability:

Cell viabilities of HCT116 and HCT-15 cell lines were tested with treatment of TAT-braftide and the TAT control peptide. Cells were seeded onto poly-lysine coated, clear-bottomed, 96-well plates at 15000 cells per well. After 24 hr, the cells were treated with TAT braftide or the TAT control peptide at different concentrations (0, 0.78, 1.56, 3.12, 6.25, 12.5, 25, 50 and 100 µM). Upon 48 hr treatment, cell viability was determined through the WST cell viability assay. According to manufacturers' instructions, 10 µL of the WST reagent was added to each well and incubated at 37° C. for 4 hrs. Absorbance readings for the plate were then taken at 450 nm in a Biotek plate reader.

Confocal Microscopy Imaging:

HEK293 cells were plated on glass plated coated with polylysine at $2.5 \times 10^5$ cells per 2 mL and allowed to adhere for 24 hr. Cells were then transfected with $BRAF^{WT}$ for 48 hr and then treated with Cy3-labeled braftide for 2 hr, followed by washing with PBS and fixing in 4% PFA (in PBS) for 15 min at RT. After fixation, cells were treated with 0.25% triton X-100 for 5 min and then blocked in 1% BSA in PBST for 30 min at RT followed by washing with PB ST. Then, cells were incubated with the anti-FLAG antibody overnight. Cells were then washed with PBS for 3×5 min and incubated with IR-dye conjugated anti-mouse for 1 hr at 37° C. and then stained with DAPI for 5 min at RT and washed with PBS for 3×5 min. Then, the plates were imaged by a confocal laser scanning microscope (Leica dmi8).

Transient Transfection into Mammalian Cells:

HEK293 cells were plated at one million cells per 2 mL :DMEM supplemented with 10% FBS and 1% L-glutarnine. These cells were incubated at 37° C. with 5% $CO_2$ for 24 hours or until the cells reach a confluency of 40-60%. DNA (1-3 µg) was mixed with PEI-MAX in a 1:3 ratio in Opti-MEM at RT for ~25 minutes and added onto the cells with fresh media. After 48 hrs, the cells were washed with cold PBS, harvested, lysed with 4% SDS and homogenized. For peptide assays, 48 hrs post-transfection, cells were treated with TAT-Braftide/TAT control in reduced serum media at the indicated concentrations for 4 hrs. The cells were then washed twice with PBS, lysed as above and quantified with the BCA protein assay. Equal amounts of cell lysates were loaded for immunoblotting and then probed for relevant proteins. For cell-based synergy assays, 48 hrs post-transfection, the cells were treated with TAT-braftide at the indicated concentration for 2 hrs. Thereafter, dabrafenib or vemurafenib were added to the cells at the indicated concentrations for 1 hr. Cells were washed twice with PBS and processed as above. Protein concentrations were determined with BCA assays for immunoblotting.

Full-Length BRAF and MEK Purification:

FL-BRAF$^{WT/G469A}$ were expressed in HEK293F cells (Wang, et al., 2017, Mol Biol 1487, 23-33; Luo, et al., 2008, J Med Chem 51, 6121-6127). The cell culture pellet was lysed in salt buffer supplemented with phosphatase and protease inhibitors, sonicated and centrifuged to obtain the supernatant. The supernatant was filtered and applied to pre-equilibrated cobalt resin for 2-3 hrs at 4° C. Resin was washed extensively with salt buffer and the protein was eluted off the resin with an imidazole gradient. Elutions were analyzed through SDS-PAGE gels, pooled and further purified through size exclusion chromatography. Similarly, kinase-dead 6×-His/MEK-(K97M)/GST protein was purified from E. coli (BL21 codon plus). Bacterial cultures were grown and induced with 0.5 mM IPTG at 16-18° C. overnight. The cell pellet was lysed in lysis buffer as indicated above, sonicated and centrifuged to obtain the supernatant and incubated with equilibrated cobalt resin 2-3 hours. The protein bound resin was washed with salt buffer as described elsewhere herein. MEK1 was eluted with imidazole buffer and further purified through size-exclusion chromatography. Proteins were concentrated and stored at −80° C. ELISA assays:

ELISA assays were adapted from Qin, et al., 2012., J Med Chem 55, 5220-5230. Glutathione-coated plates were conditioned in HTBS buffer (25 mM HEPES pH 7.4, 140 mM NaCl, 0.05% Tween-20). The plates were incubated with GST-tagged, kinase-dead, MEK (0.0025 mg mL-1) for >2 hr with shaking. Appropriate concentrations of the peptide were made and pre-incubated with BRAF$^{WT/G469A}$ (5 nM final) full-length protein for 90 min. After 2 hr, the MEK solution was washed away and replaced with an ATP kinase buffer (25 mM HEPES pH 7,4, 150 mM NaCl, 20 mM $MgCl_2$, 50 mM glycerol phosphate, 40 µM ATP). The BRAF/peptide mixture was then added to the ATP-cocktail (1:1) and the kinase reaction was allowed to proceed for 15 min at 30° C. Thereafter, the reaction mixture was washed away and sequentially incubated with the primary antibody (pMEKS217/221) for 1 hr, followed by secondary antibody (anti-rabbit, LI-COR) for 1 hr. After final washing steps, the chemiluminescent agent (Pierce) was added to the wells and the luminescence was measured on a Biotek plate reader.

TABLE 1

| List of materials reagents, antibodies used for experiments. | | |
|---|---|---|
| Reagent or Resource | Company | Catalog Number |
| Antibodies | | |
| Mouse monoclonal anti-FLAG | Sigma | F1804-1MG |
| Mouse monoclonal Anti-Actin | Sigma | A1978-200 |
| Rabbit monoclonal anti-pMEK | Cell Signaling Technology | 9154S |
| Rabbit monoclonal anti-pERK | Cell Signaling Technology | 4370S |
| Mouse monoclonal anti-MEK | Cell Signaling Technology | 4694S |
| Mouse monoclonal anti-ERK | Cell Signaling Technology | 74696S |
| HRP-conjugated anti-rabbit | Cell Signaling Technology | 7074S |
| HRP-conjugated anti-mouse | Cell Signaling Technology | 7076S |
| IR-conjugated anti-rabbit | LI-COR | 926-3211 |
| IR-conjugated anti-mouse | LI-COR | 926-68070 |

TABLE 1-continued

List of materials reagents, antibodies used for experiments.

| Reagent or Resource | Company | Catalog Number |
| --- | --- | --- |
| Cell Culture and Transient Transfections | | |
| Dulbecco's Modified Eagle Medium | Gibco | 11995-065 |
| Phosphate-buffered saline | Gibco | 10010-023 |
| Fetal bovine serum | Gemini Bio-Products | 100-602 |
| L-glutamine | Gibco | 25030-081 |
| Trypsin-EDTA | Gibco | 25300-054 |
| Opti-MEM reduced serum media | Gibco | 31985-070 |
| Polyethyleneimine | Polysciences, Inc. | 24765 |
| Protein Quantification and Immunoblotting | | |
| Bicinchoninic acid kit | Thermo Scientific | 23225 |
| Bovine serum albumin | Sigma-Aldrich | A7906-500G |
| Nitrocellulose membranes | Bio-Rad | 1620115 |
| Inhibitors | | |
| Debrafenib | SelleckChem | S2807 |
| Vemuraferib | SelleckChem | S1267 |
| Trametetinib | SelleckChem | S2673 |
| Cycloheximide | Sigma-Aldrich | C1988-1G |
| Bortezomib | SelleckChem | S1013 |
| Peptides | | |
| Braftide | Lifetein | Custom |
| Null-Braftide | Lifetein | Custom |
| TAT-PEGlinker-Braftide | Lifetein | Custom |
| TAT | Lifetein | Custom |
| Plasmids | | |
| BRAF-WT-FL | | |
| BRAF-G469A-FL | | |
| MEK-K97M | | |
| ELISA Material | | |
| ELISA-glutathione-coated plates | Pierce-ThermoFisher | 15420 |
| SuperSignal ™ ELISA Pico Chemiluminescent Substrate | ThermoFisher Scientific | 37070 |

Example 1

Computational Peptide Design Targeting the DIF of BRAF

Structural analyses of dimeric BRAF reveal key features of the DIF, which provide an excellent starting point for designing inhibitors targeting this interface (Rajakulendran, et al, 2009, Nature 461, 542-545). The sequence of the human serine/threonine-protein kinase BRAF (Accession Number: P15056) was obtained from the UniProtKB database and used as the query sequence to search the PDB database using the FASTA search engine (ebi dot ac dot uk). For the FASTA search, the parameter for both the Scores and Alignments was set to 2000. The PDB list of all the hits having >99% sequence identity with the query sequence was then crossed checked with the PDB list in the Supplementary Table 1 of Thevakumaran, et al., 2014, *Nature Structural & Molecular Biology* 22, 37-43.

In the Supplementary Table 1 of Thevakumaran, et al., 33 BRAF kinase domain dimer structures were classified in two categories: 26 on-state structures and 7 off-state structures. From those structures shown on both PDB lists, one representing the on-state (PDB ID: 1UWH) and one representing the off-state (PDB ID: 3TV6) were chosen randomly. Next, these two chosen structures (PDB ID: 1UWH and 3TV6) were subjected to the ROSIE PeptiDerive searching engine (rosie dot rosettacommons dot org/peptiderive). For a given protein-protein complex structure, PeptiDerive identifies peptide segments that contribute most to the protein-protein interaction. The derived peptide length was set from 5 to 10. From the output results, the peptide sequence with the highest Relative Interface Score (%) was identified. A series of peptides that contribute most to the protein-protein interaction were selected from the output results of the input structure (PDB ID: 1UWH and 3TV6), Table 2.

TABLE 2

Top ranked peptides through PeptiDerive analysis with their relative contributing scores.

| No. | Input Structure (PDB ID) | Peptide Sequences | Relative Interface Score (%) |
| --- | --- | --- | --- |
| 1 | 1UWH | RKTRHVNILL SEQ ID NO: 8 | 46.30% |
| 2 | 1UWH | CRKTRHVNILLC (cyclic peptide through cystine formation) SEQ ID NO: 9 | 46.30% |
| 3 | 3TV6 | TRHVNILLFM SEQ ID NO: 1 | 46.91% |

Example 2

Evaluation of the Peptide Inhibitors Against Wild-Type BRAF and Oncogenic BRAF$^{G469A}$ The selected peptides were then subjected to a rapid and robust ELISA to measure the $IC_{50}$ values of these peptides against full-length (FL) BRAF$^{WT}$ and FL-BRAF$^{G469A}$ which were purified from HEK293F cells. Different from the isolated catalytic domain which is dominantly monomeric in solution, purified FL-BRAF protein adopts an active dimeric configuration in solution, therefore it is advantageous to evaluate dimer breaker inhibitors using purified FL-BRAF. The G469A mutation was chosen as the representative of non-V600 mutations, as it is the most prevalent non-V600 BRAF mutation identified in lung cancer. In addition, the G469A variant is dependent on the integrity of the dimer interface.

Figure 1B:
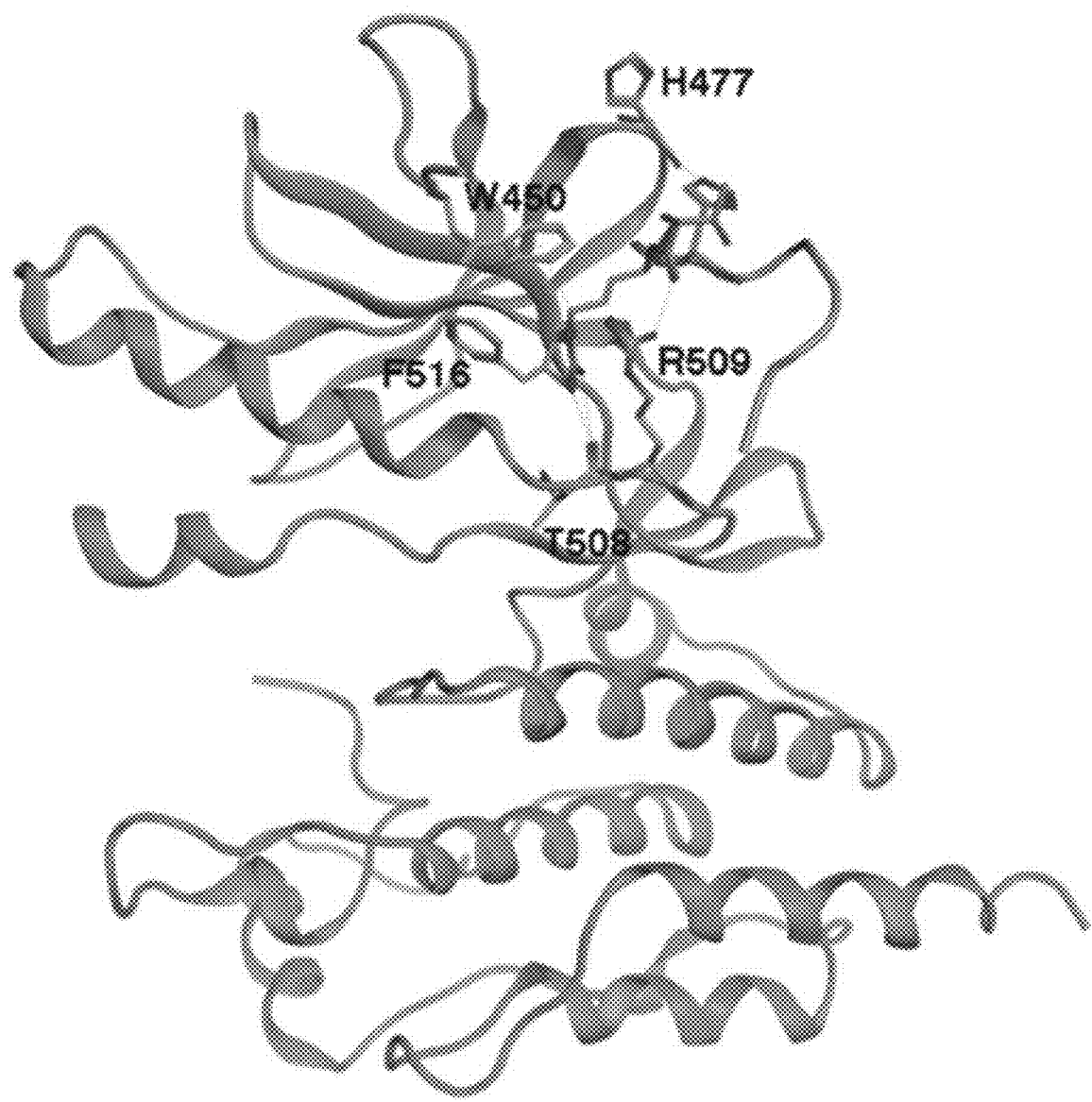
Figure 1C:
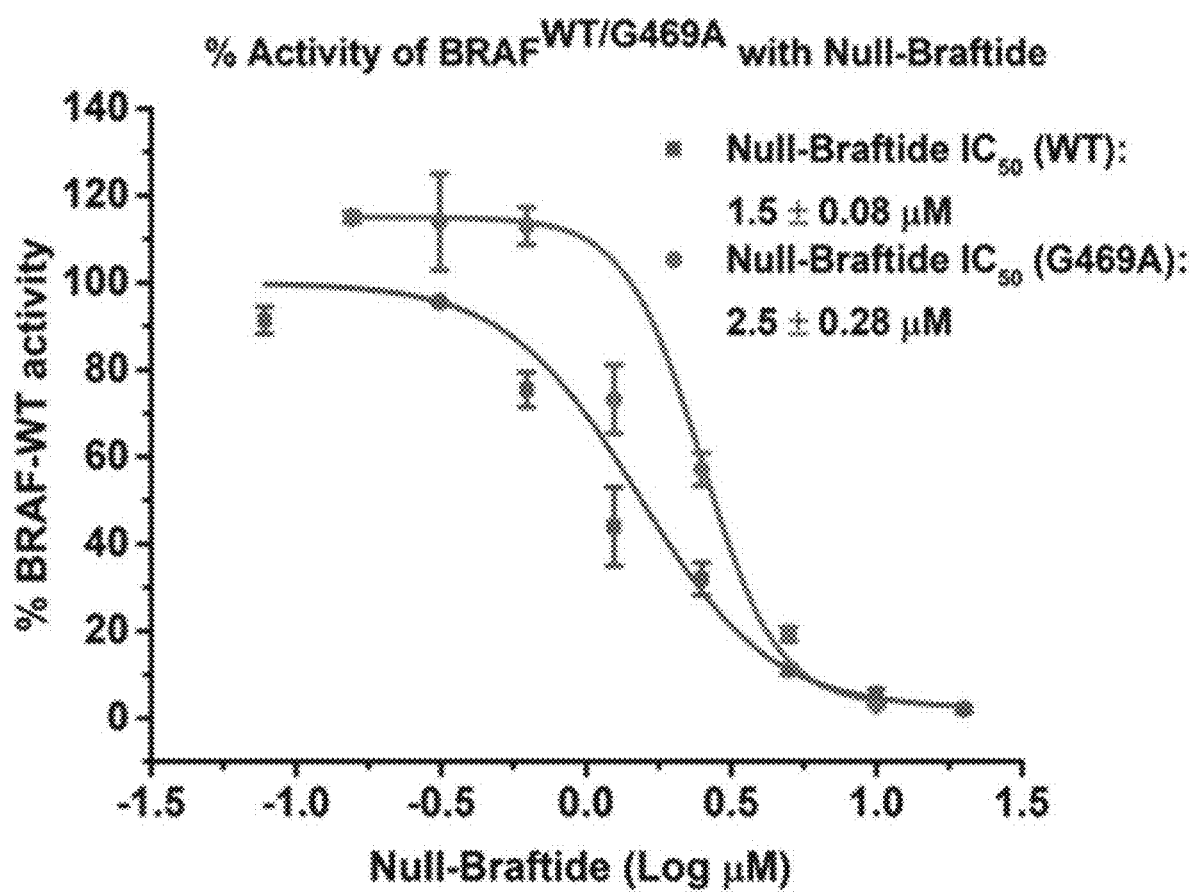

One 10-mer peptide, whose sequence (TRHVNILLFM; SEQ ID NO:1) is derived from the dimer interface of BRAF, showed the most potent inhibition, with IC$_{50}$ values of 364 nM against wild-type BRAF and 172 nM against oncogenic BRAF$^{G469A}$ (FIG. 1A). This peptide was named as braftide. Upon computational docking, braftide was found to bind predominantly at the dimer interface of BRAF kinase domain (FIG. 1B), in which the Arg amino acid of braftide is participating in binding to BRAF. Arg was mutated to His and a control peptide named as null-braftide (THHVNILLFM; SEQ ID NO:48) was generated. As shown in FIG. 1C, null-braftide curves demonstrated a right shift to those for braftide, with increased IC$_{50}$ values of 1.5 µM (~4-fold increase) and 2.5 µM (~15-fold increase) for wild-type and G469A, respectively, which reflects the reduced binding affinity of the null-braftide for BRAF, suggesting that Arg is involved in peptide/protein interaction, as predicted by the model (FIG. 1B).

Figure 1D:
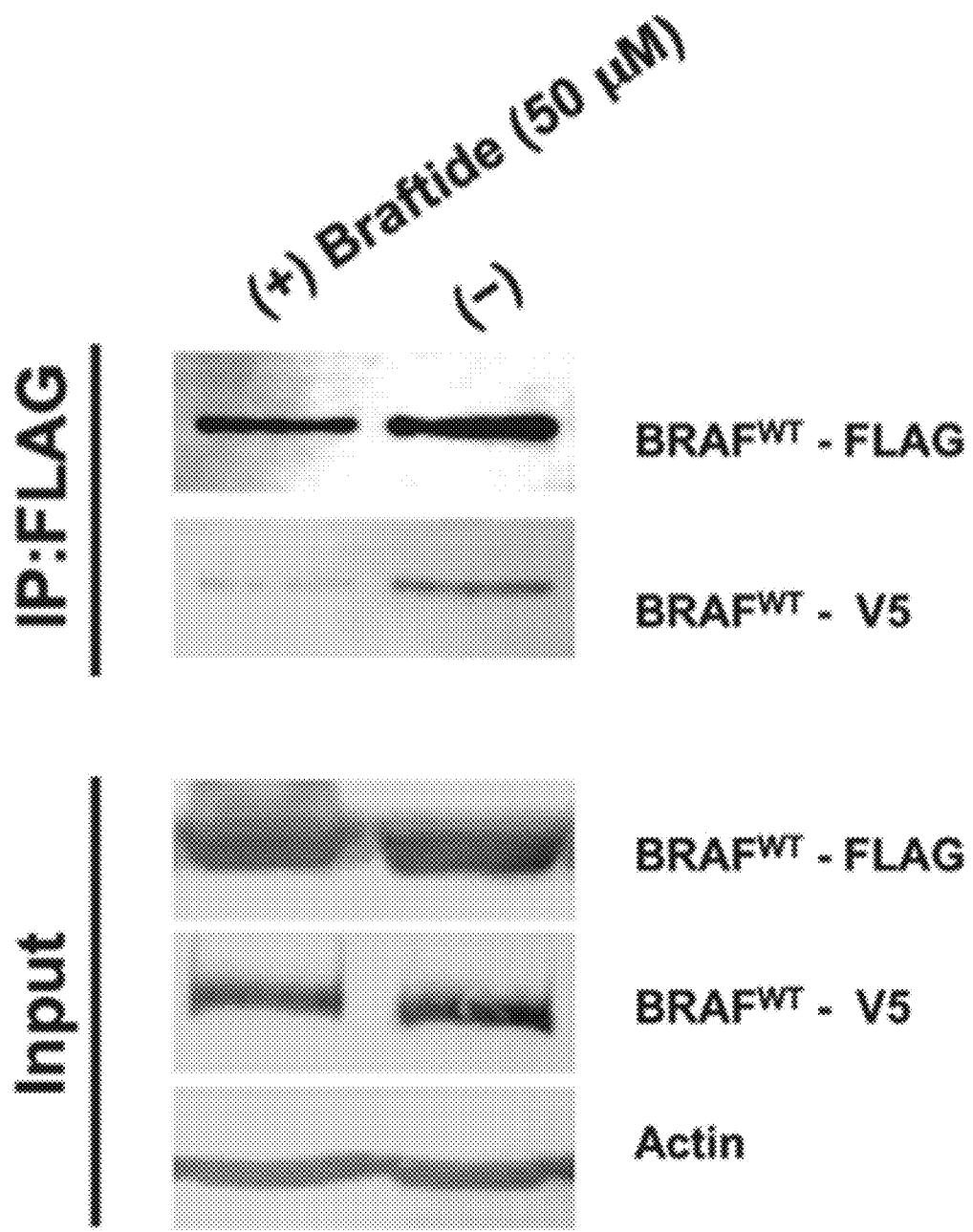

Next, the ability of braftide to disrupt BRAF homodimers was evaluated. In the co-immunoprecipitation experiment, FLAG-tagged BRAF and V5-tagged BRAF were coexpressed in HEK293 cells. Cell lysate was subjected to Flag antibody-conjugated resin, which was later probed for V5-tagged BRAF. As shown in FIG. 1D, adding 50 µM of braftide to cell lysate decreased the formation of BRAF homodimers, consistent with the hypothesis that braftide disrupts BRAF dimers. Overall, the data suggested that braftide allosterically inhibits BRAF activation by blocking formation of the BRAF dimer.

Example 3

Delivery of Braftide into HEK293 Cells Decreases MAPK Signaling

Figure 2A:
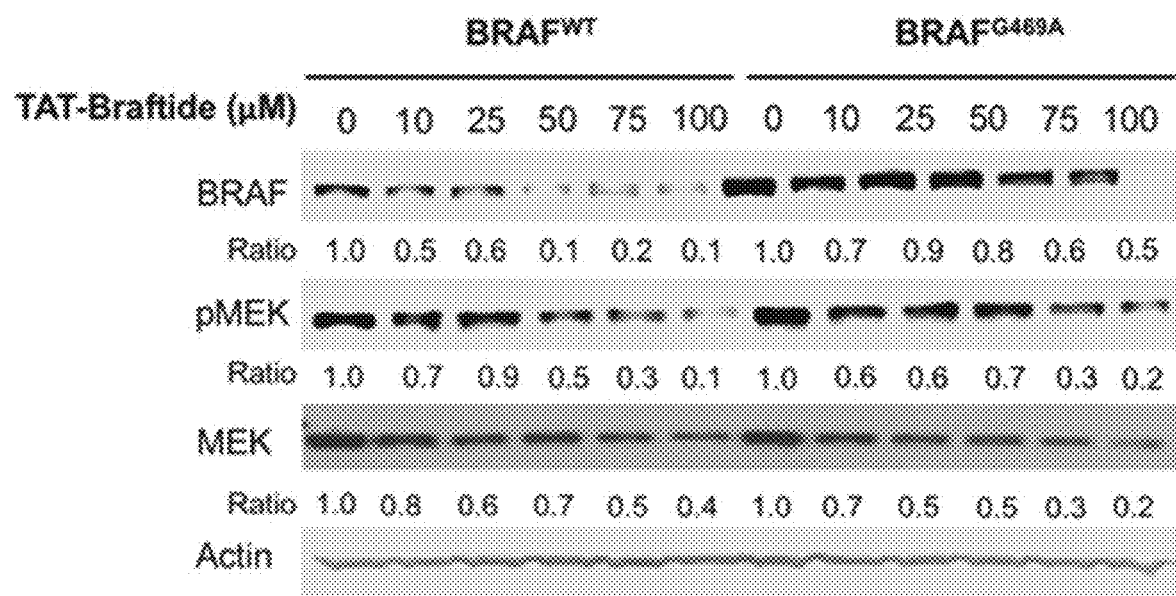
Figure 2B:
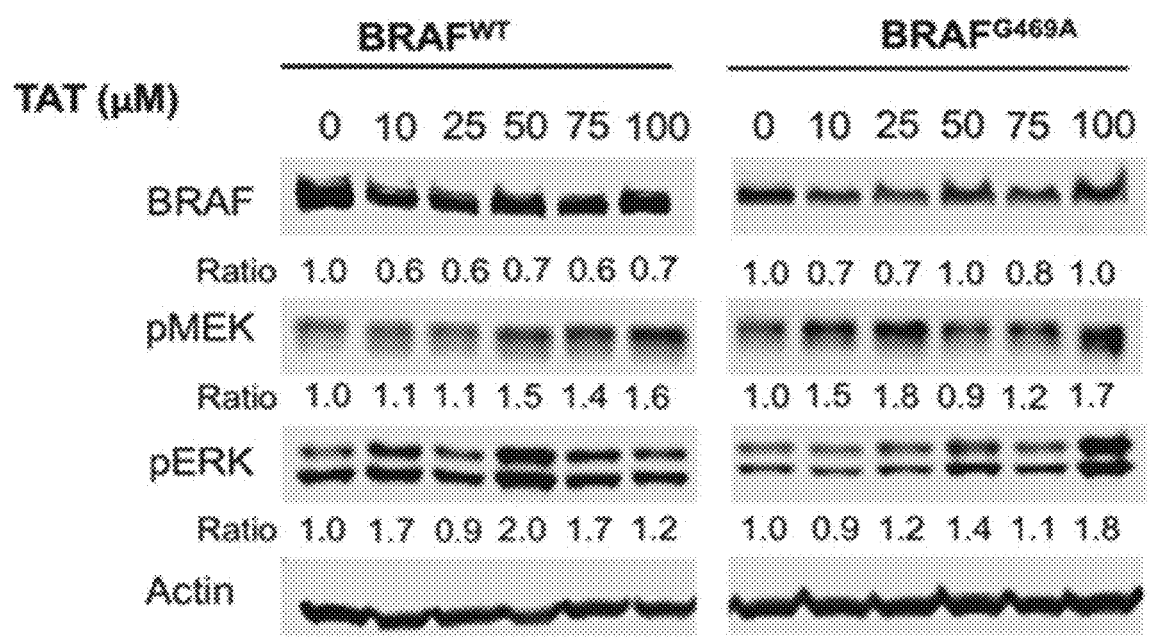
Figure 7:
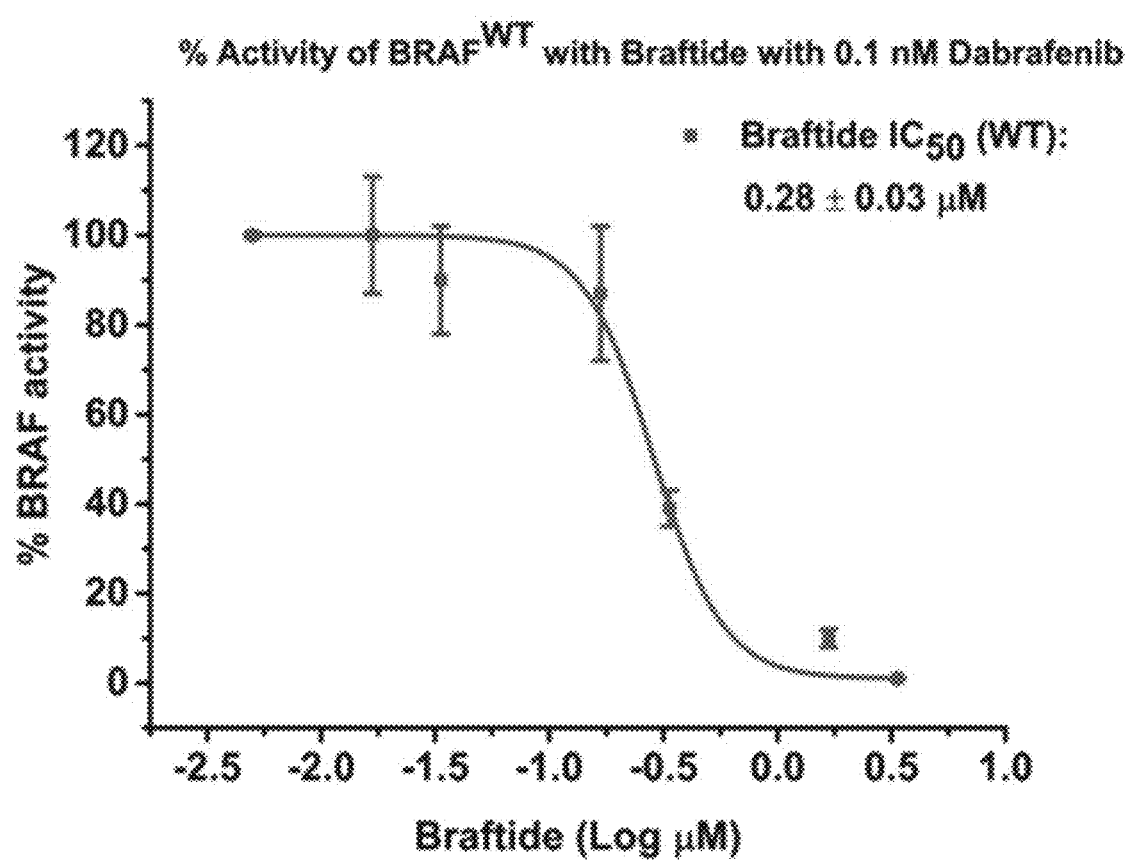
FIG. 7 is a graph showing that addition of the TAT cell permeability tag has no adverse effect on the $IC_{50}$ against $BRAF^{WT}$. Error bars represent standard deviations of triplicate measurements. Dose-response curves were generated in Origin and IC50 was calculated with a 4-parameter logistic function.

Braftide was conjugated with the TAT sequence (GRKKRRQRRRPQ; SEQ ID NO:2), a cell-penetrating peptide widely used in peptide drugs. In vitro enzyme assays demonstrate that the addition of TAT sequence has no effect on the inhibition potency of braftide (FIG. 7). HEK293 cells were transiently transfected with plasmid encoding either wild-type BRAF or BRAF$^{G469A}$. 48 hr post-transfection, the cells were treated with various concentrations of TAT-braftide. In parallel, TAT peptide was used as the negative control. The activity of BRAF was quantified by probing for phospho-MEK1/2. Actin is used as the loading control. Consistent with the in vitro kinase assays, treatment with TAT-braftide significantly reduced the activity of BRAF in a dose-dependent manner (FIG. 2A). In contrast, no inhibition effect was observed for TAT control peptide in transiently transfected HEK293 cells (FIG. 2B). A Cy3-tagged version of braftide was synthesized and evaluated for its ability of crossing the plasma membrane using immunofluorescence experiments. HEK293 cells were treated with braftide-Cy3 or vehicle control. Cells were then fixed and stained for immunofluorescence. Internalization of the peptide through the Cy3-tagged braftide was confirmed (FIG. 2C).

Example 4

Braftide Triggers Protein Degradation of BRAF and MEK

Intriguingly, the protein levels of overexpressed BRAF and endogenous MEK1 were markedly decreased in a dose-dependent manner upon TAT-braftide treatment (FIG. 2A). Dimerization of RAF significantly augments the expression level of RAF proteins in HEK293 cells.

Figure 3A:
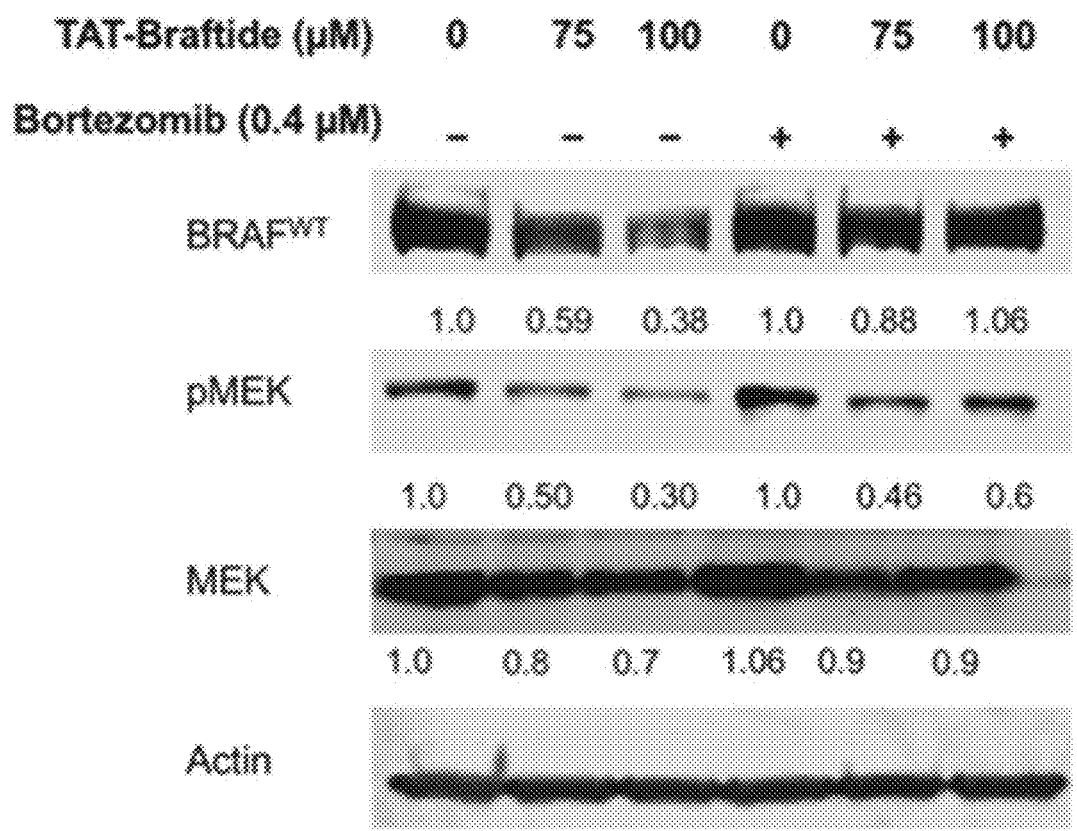
FIGS. 3A-3D illustrate BRAF degradation with TAT-braftide treatment rescued through proteasome inhibition.
Figure 3B:
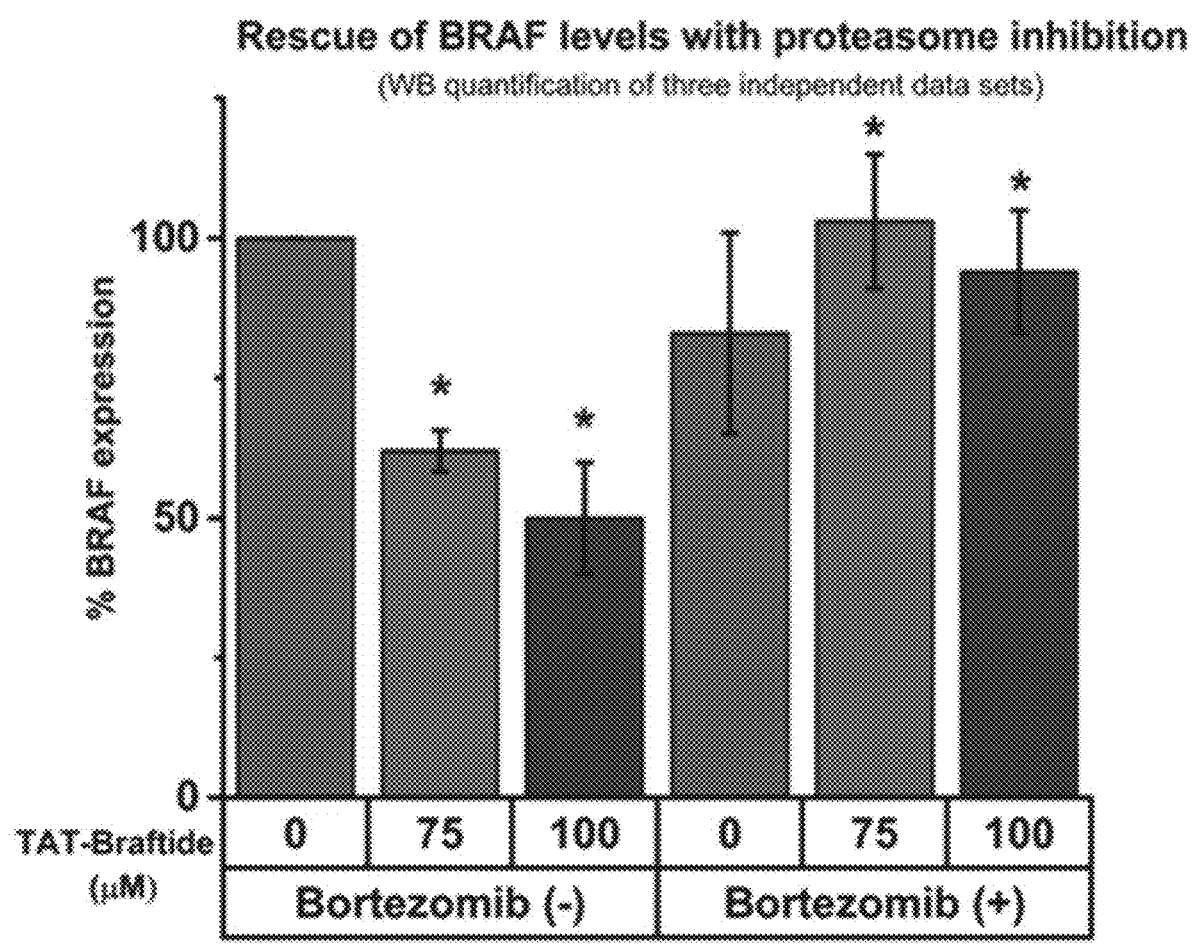
Figure 3C:
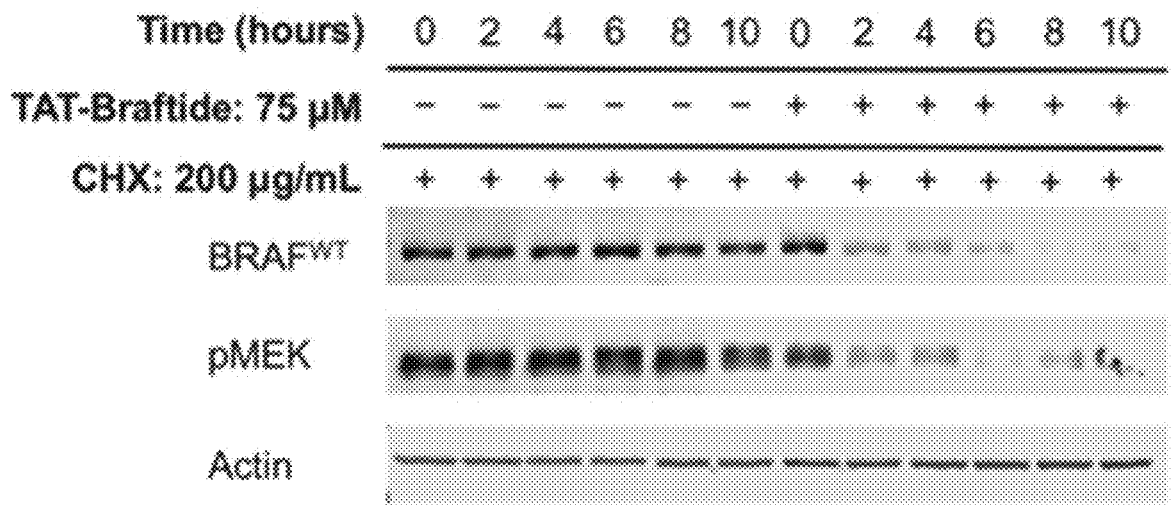
Figure 3D:
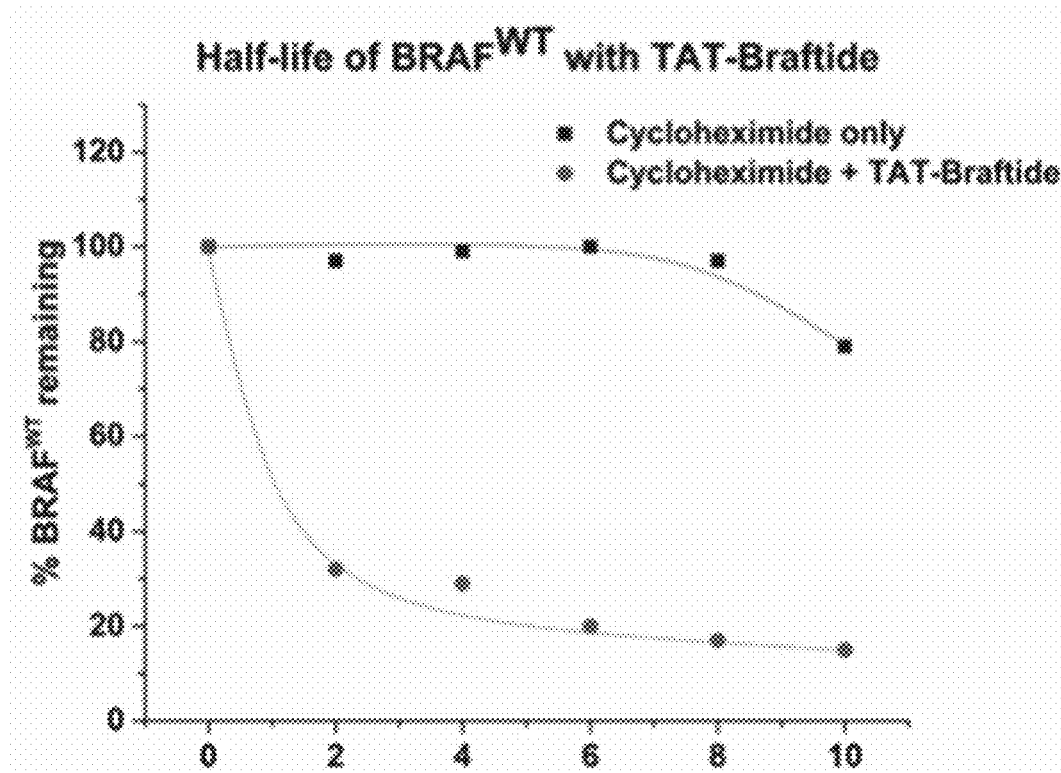

In certain embodiments, TAT-braftide not only exerts an inhibitory effect but also triggers proteolysis of BRAF and MEK by disrupting BRAF dimerization in HEK293 cells. In light of this, HEK293 was pre-treated cells with proteasome inhibitor bortezomib before adding TAT-braftide. As shown in FIGS. 3A and 3B, although proteasome inhibition rescues BRAF from protein degradation, TAT-braftide still successfully inhibited the kinase activity of BRAF, suggesting that the diminished MAPK signaling upon braftide treatment is due to the dual function of braftide: inhibiting the kinase activity of BRAF while inducing proteasome-mediated protein degradation, the latter reflects the non-catalytic function of BRAF. To evaluate the potent induction of degradation, the half-life of BRAF protein was compared in the presence and absence of braftide. HEK293 cells transiently transfected with wild-type BRAF were treated with cycloheximide. Braftide treatment reduced the half-life of BRAF from >10 h to ~2 h (FIGS. 3C and 3D). Together, this data support that disruption of the dimerization interface with a peptide inhibitor sequesters BRAF in an inactive state to induce degradation of the MAPK complex.

Example 5

Braftide is Potent Against BRAF/CRAF Heterodimers and p61 BRAF$^{V600E}$ Dimers

Figures 4A, 4B:
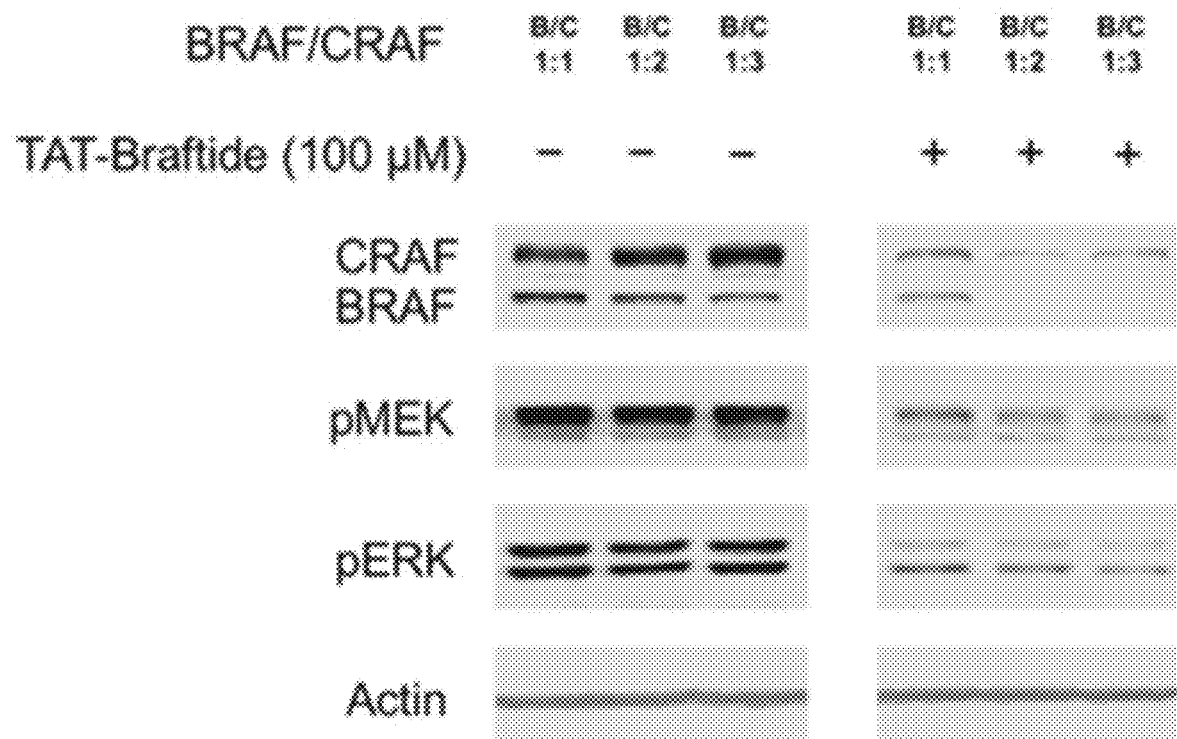
FIGS. 4A-4C illustrate TAT-braftide inhibits the Kinase Activity of BRAF/CRAF Heterodimer in HEK293 Cells.
Figure 4C:
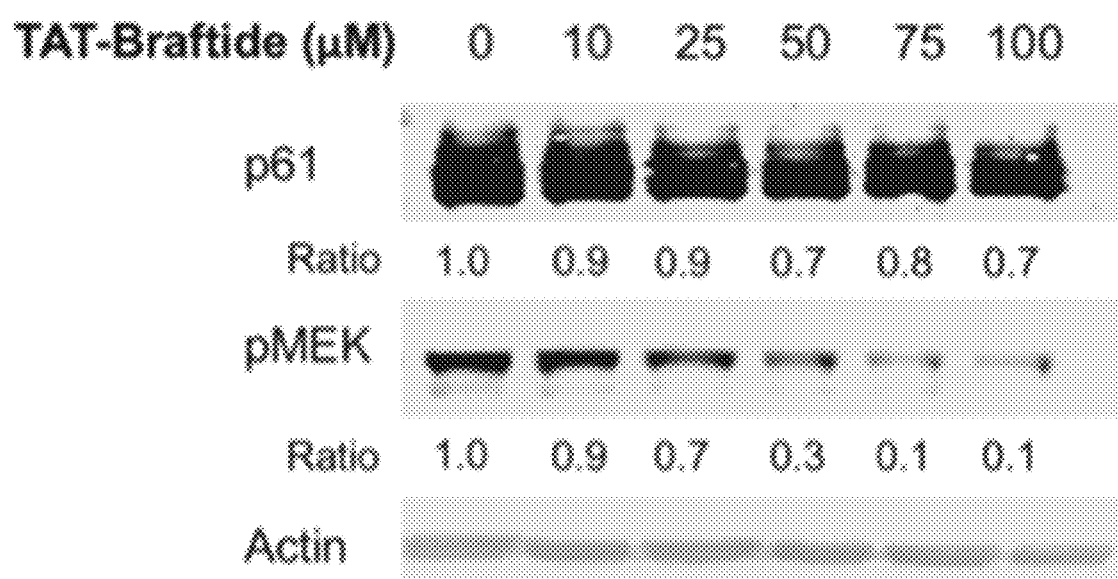
Figure 8:
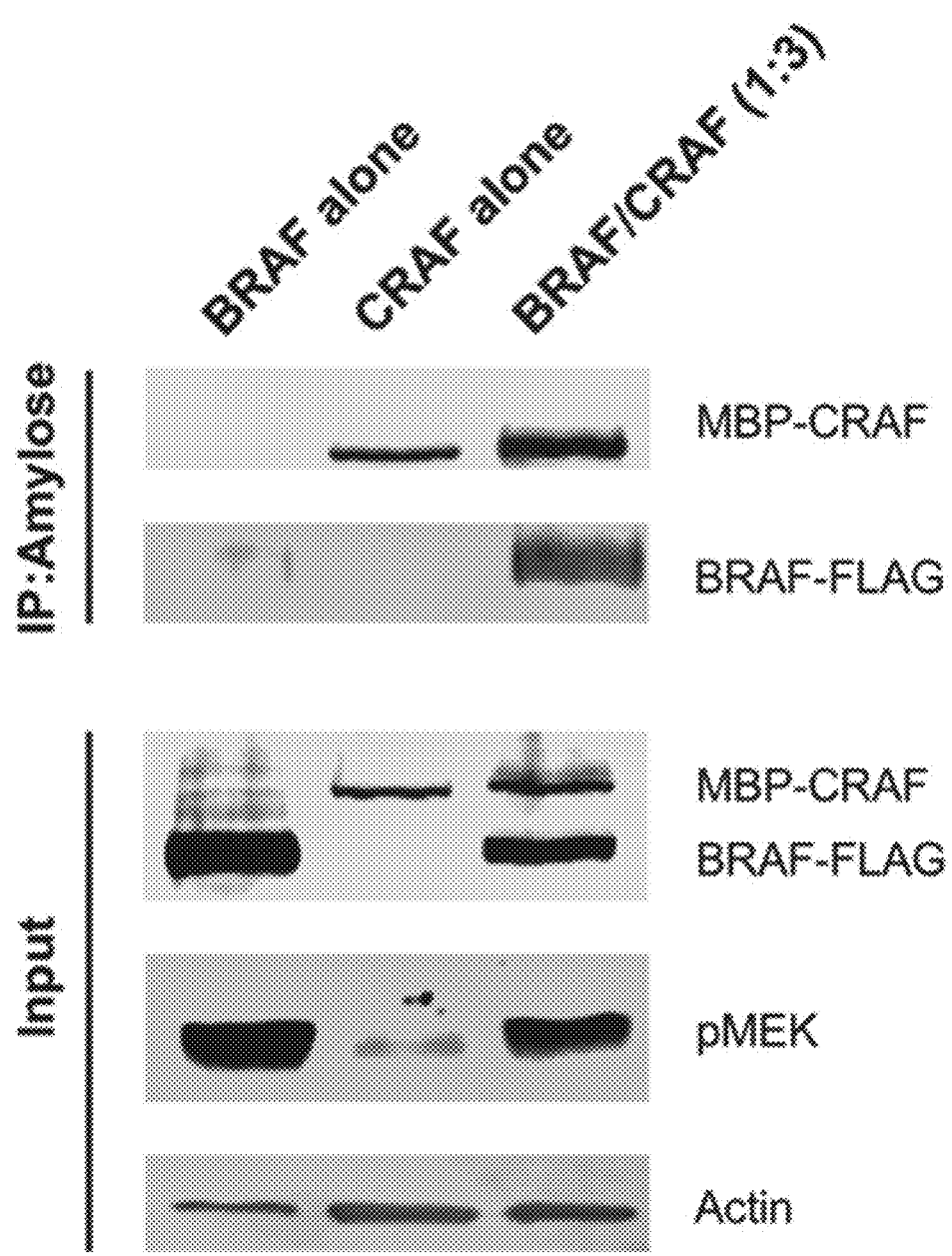
FIG. 8 illustrates-immunoprecipitation of BRAF-FLAG with MBP-CRAF. HEK293 cells were transfected with BRAF, CRAF and BRAF/CRAF (1:3 ratio). Cell lysates were subjected to pull-down with amylose resin. Samples were analyzed through immunoblotting for MBP-CRAF and BRAF-FLAG.
Figure 9:
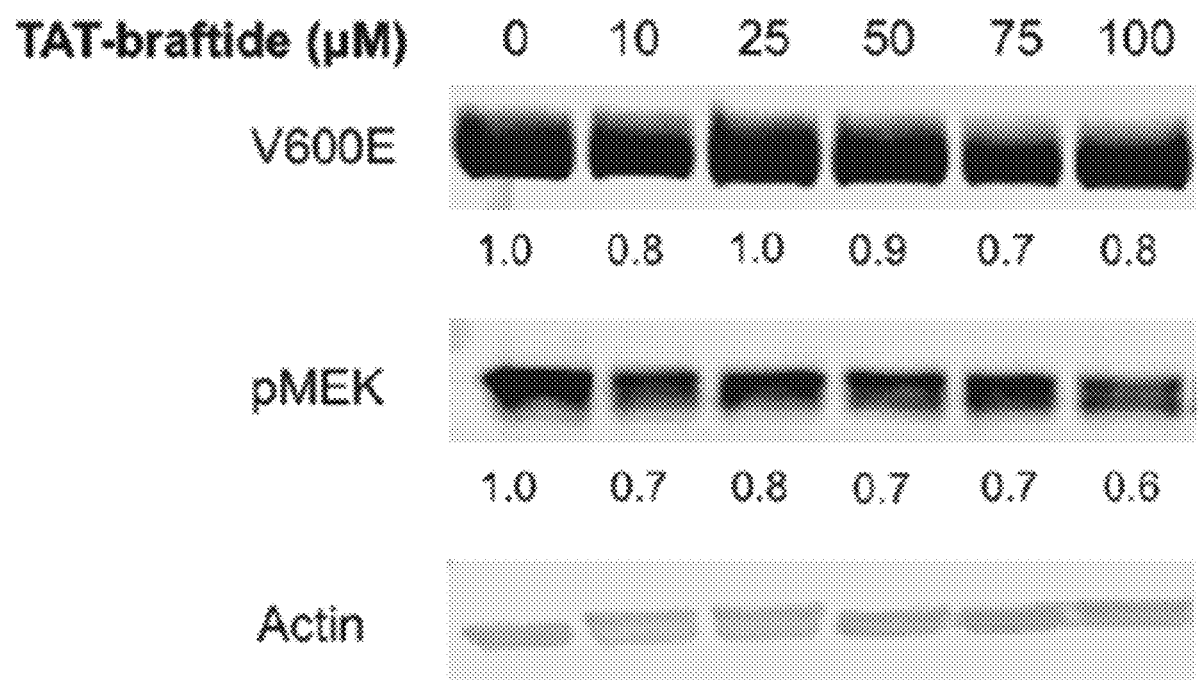
FIG. 9 illustrates evaluation of the inhibition effect of braftide on BRAFV600E. HEK293 cells were transfected with BRAFV600E and treated with TAT-braftide at the indicated concentrations for 4 hr. Cell lysates were immunoblotted for the relevant proteins. Western blots are representative of at least three independent experiments.

The BRAF/CRAF heterodimer has been identified as the most active RAF dimer. Formation of BRAF/CRAF dimers is the major culprit of drug resistance and paradoxical activation, two major limitations of current BRAF drugs. The dimer interface of the three RAF isoforms were aligned and it was found that the dimer interface is highly conserved among the RAF kinase family (FIG. 4A), which is also supported by the available BRAF and CRAF structures. In light of this, the inhibition potential of braftide against BRAF/CRAF heterodimers overexpressed in HEK293 cells was evaluated. Co-IP experiments support that BRAF and CRAF form heterodimers under the same conditions (FIG. 8). Upon braftide treatment, both BRAF and CRAF were degraded together with diminished MAPK signaling (FIG. 4B), suggesting that the BRAF/CRAF heterodimer is sensitive to braftide as well. The activity of TAT-braftide on p61 BRAF$^{V600E}$ (FIG. 4C) and BRAF$^{V600E}$ was also investigated (FIG. 9). p61 BRAF$^{V600E}$ is an aberrantly spliced version of BRAF that is approximately 61 kDa in size. p61 shows constitutive dimerization capability in cell lines and is one common mechanism by which BRAF$^{V600E}$ melanoma patients acquire resistance to ATP-competitive inhibitors. Spliced BRAF$^{V600E}$ is a RAS-independent dimer but can signal ERK either as a monomer or dimer. p61-BRAF$^{V600E}$ was transiently transfected in HEK293 cells and treated them with increasing concentrations of TAT-braftide. A decrease in both pMEK and pERK levels was observed consistent with downregulated MAPK signaling, although the protein level of p61 was not affected as dramatically as wild-type BRAF (FIG. 4C). Conversely, braftide inhibits BRAF$^{V600E}$ to a much lesser extent (FIG. 9), suggesting that p61 and BRAF$^{V600E}$ have distinct activation mechanisms.

Example 6

Evaluation of the Synergy Between Braftide and ATP-Competitive BRAF Inhibitors

Figure 5A:
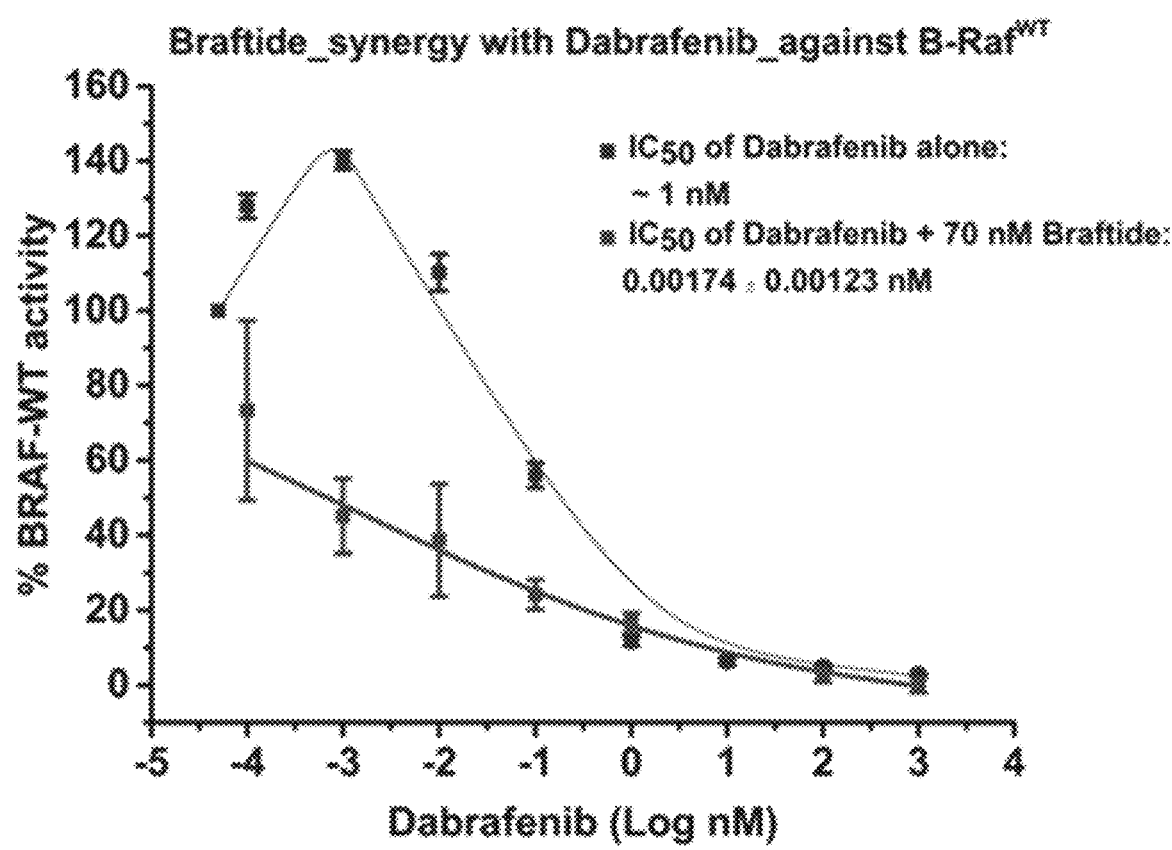
FIGS. 5A-5D illustrate combination treatment of braftide and dabrafenib abrogates paradoxical activation and improves dabrafenib efficacy.
Figure 5B:
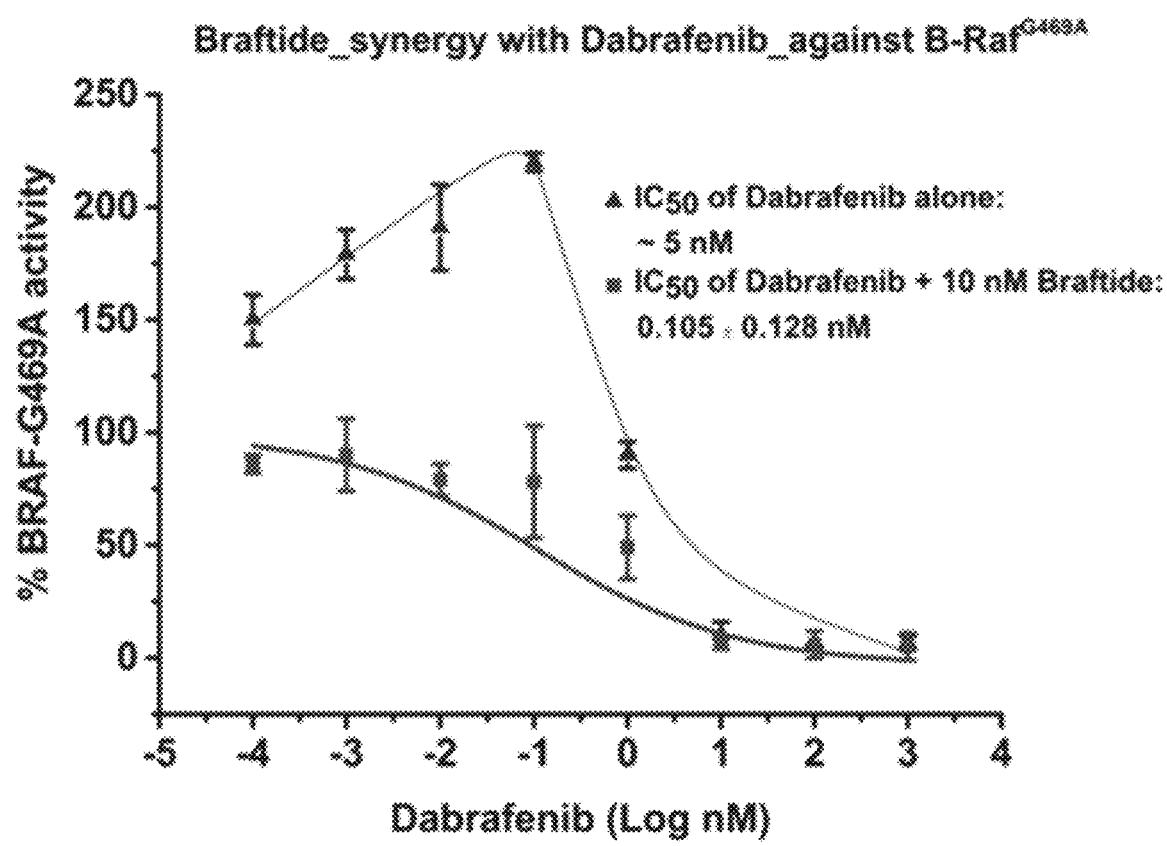
Figure 5C:
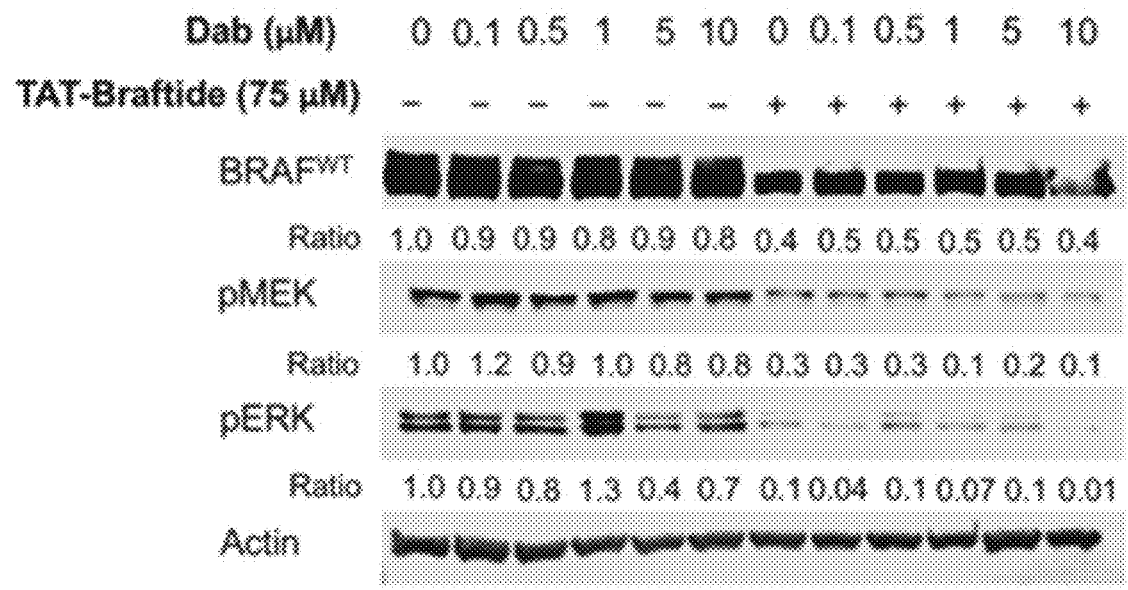
Figure 5D:
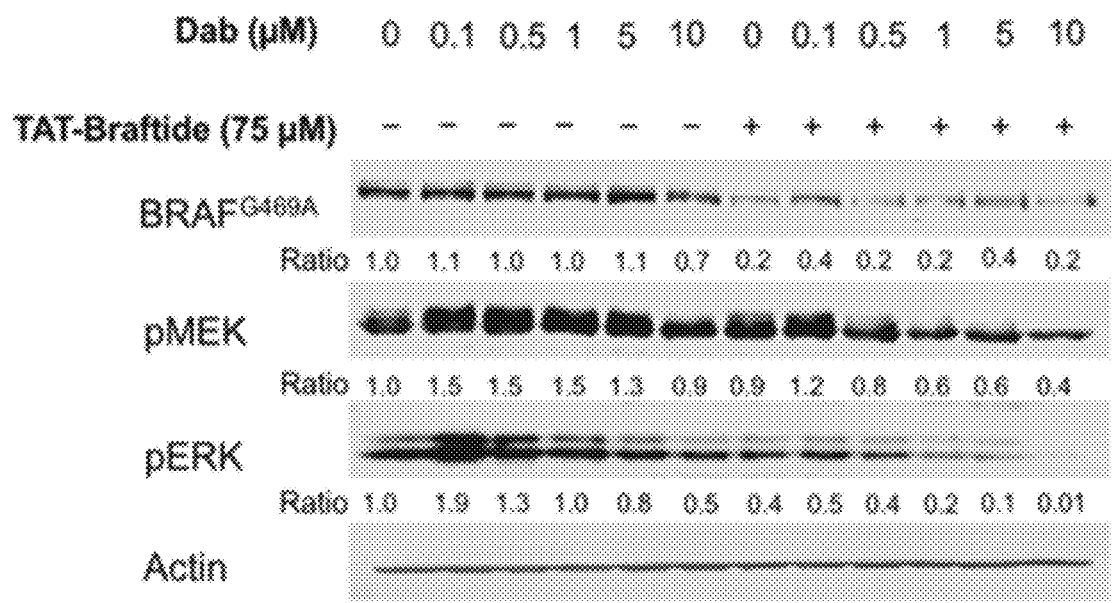

The efficacy of current ATP-competitive BRAF inhibitors is limited to BRAF$^{V600E}$ that signals as a monomer. Inhibition of BRAF dimers by dabrafenib and vemurafenib is limited by induction of negative cooperativity within a dimer in which the inhibitor-bound protomer allosterically activates the inhibitor-free protomer to cause drug resistance and paradoxical activation. Braftide is designed to dissociate BRAF dimers, thus braftide may synergize with ATP-competitive inhibitors to potently inhibit dimeric BRAF, expanding the application of current BRAF therapies to all BRAF variants. The IC$_{50}$ values of dabrafenib against purified FL-BRAF in the presence and absence of braftide was evaluated. As shown in FIG. 5A, the IC$_{50}$ value of dabrafenib against dimeric wild-type BRAF was decreased ~1000-fold after pre-incubating BRAF with 70 nM of braftide. Moreover, the notorious 'paradoxical activation' caused by dabrafenib monotherapy at subsaturating concentrations was abolished by braftide (FIG. 5A). In the presence of much lower concentration of braftide (10 nM), the IC$_{50}$ value of dabrafenib against BRAF$^{G469A}$ was decreased from ~5 nM to 0.1 nM (50-fold decrease) and the paradoxical activation was eliminated by braftide (FIG. 5B). The synergy effect was further evaluated in HEK293 cells overexpressing either wild-type BRAF or BRAF$^{G469A}$. As shown in FIG. 5C, dabrafenib alone activated the MAPK signaling at lower concentrations and only performed as an inhibitor at concentrations above 10 μM, validating that dabrafenib could not potently inhibit BRAF homodimers because it triggers negative cooperativity and paradoxical activation. Pre-treatment of HEK293 cells with 75 μM of braftide for 2 h abrogated the paradoxical effect caused by lower doses of dabrafenib. A similar pattern was observed for BRAF$^{G469A}$ (FIG. 5D).

Figure 10A:
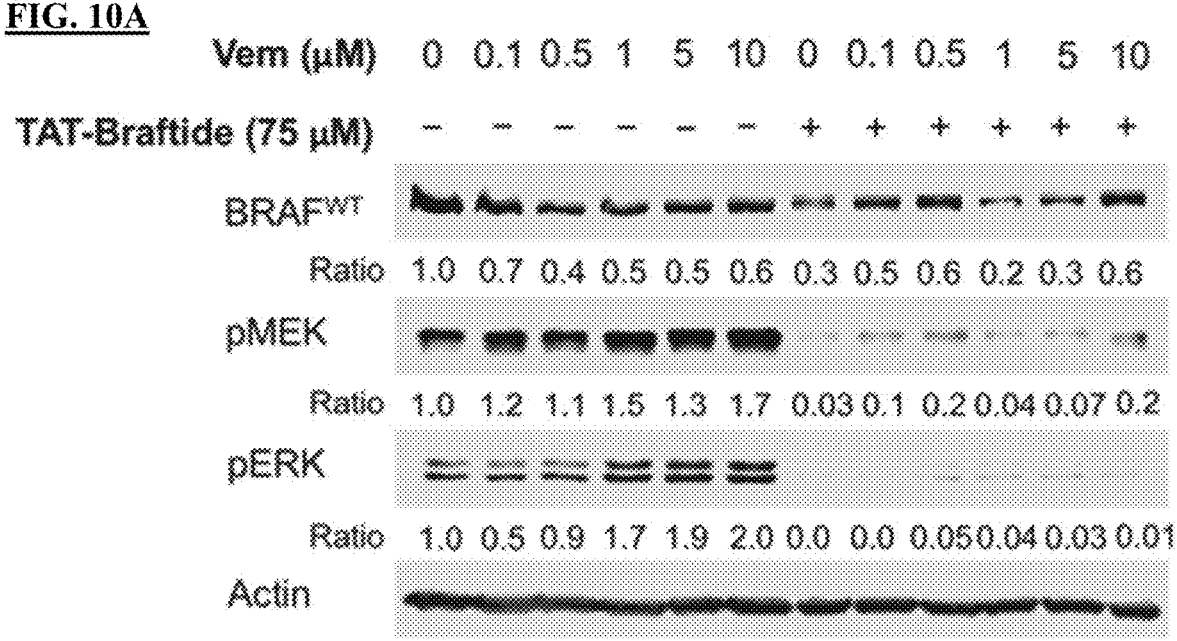
FIGS. 10A-10B illustrate effect of combination treatment of TAT-braftide and vemurafenib against BRAFG469A. HEK293 cells transiently transfected with BRAFWT/G469A were pre-treated with braftide (75 μM) for 2 hr and then vemurafenib was added at the indicated concentrations for 1 hr. Cell lysates were subjected to immunoblotting for the indicated proteins.
Figure 10B:
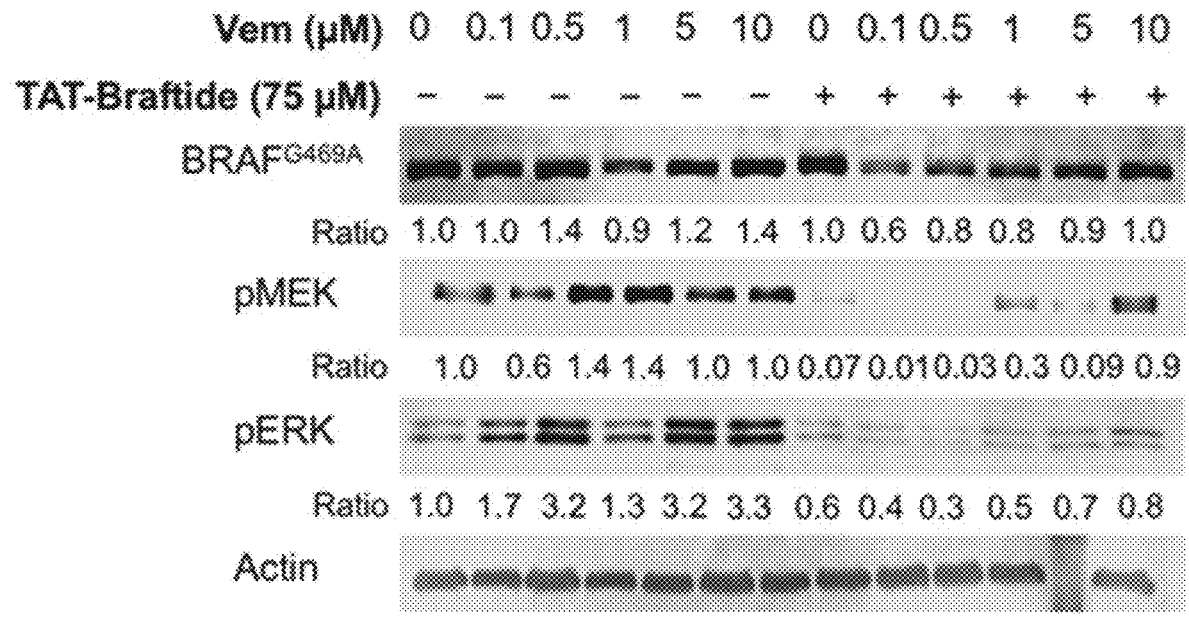
Figure 11:
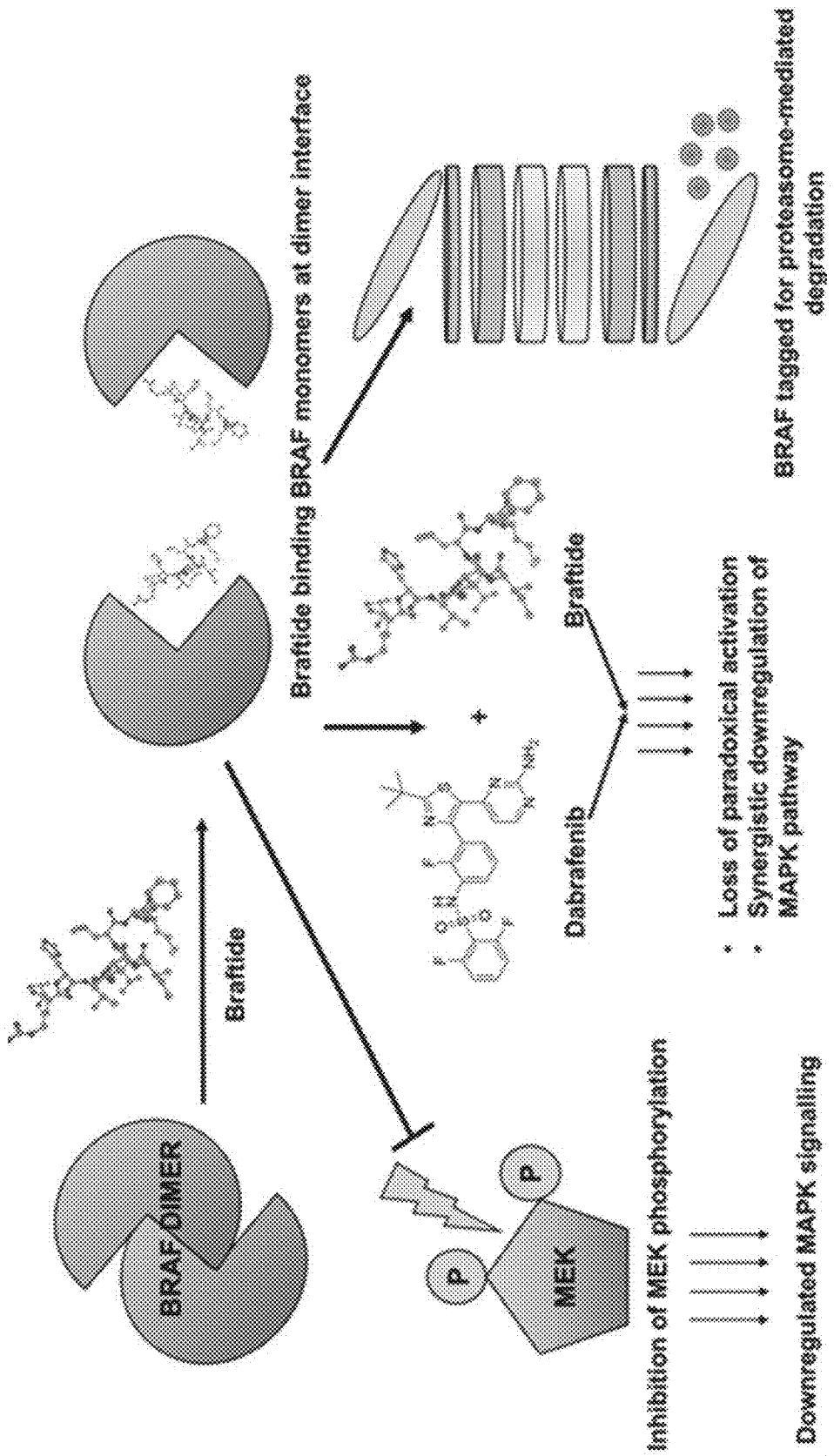
FIG. 11 illustrates non-limiting consequences of braftide binding to BRAF dimer interface.

Dabrafenib more significantly activated both MAPK signaling in HEK293 cells expressing BRAF$^{G469A}$ and purified FL-BRAF$^{G469A}$ (FIG. 5D), demonstrating that extra caution should be taken when targeting non-V600 BRAF mutants with ATP-competitive inhibitors. On the other hand, disruption of the dimer interface of BRAF proves to be a very promising strategy to eliminate the major drawbacks of ATP-competitive inhibitors. The same synergy effect between vemurafenib and braftide was validated (FIGS. 10A and 10B). These experiments demonstrated that braftide and FDA-approved ATP-competitive inhibitors work in synergy to diminish paradoxical activation and sufficiently inhibit MAPK signaling in HEK293 cells.

Example 7

Evaluation of Antiproliferative Activity of Braftide on Cancer Cells

Figure 6A:
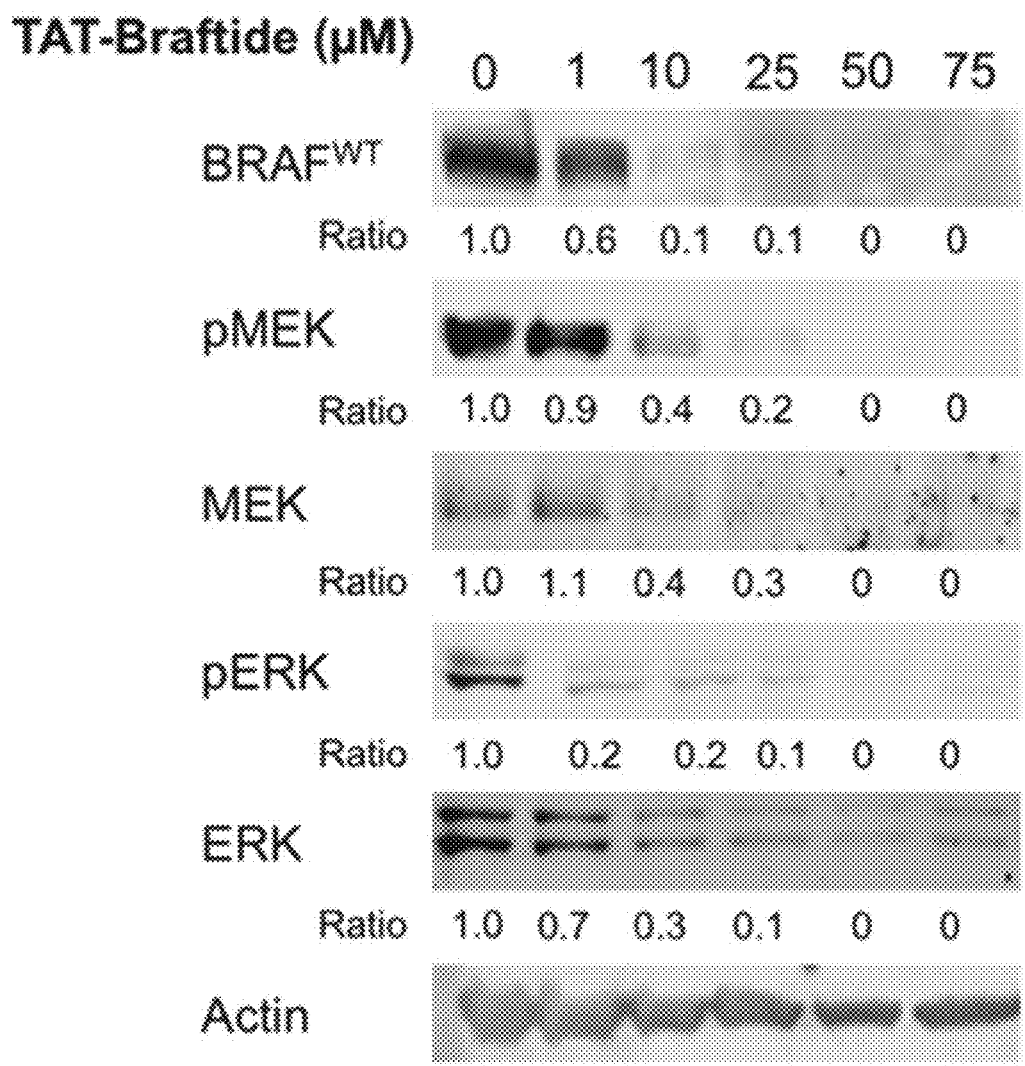
FIGS. 6A-6C illustrate braftide inhibits MAPK signaling and cell proliferation in KRAS mutated cell lines.
Figure 6B:
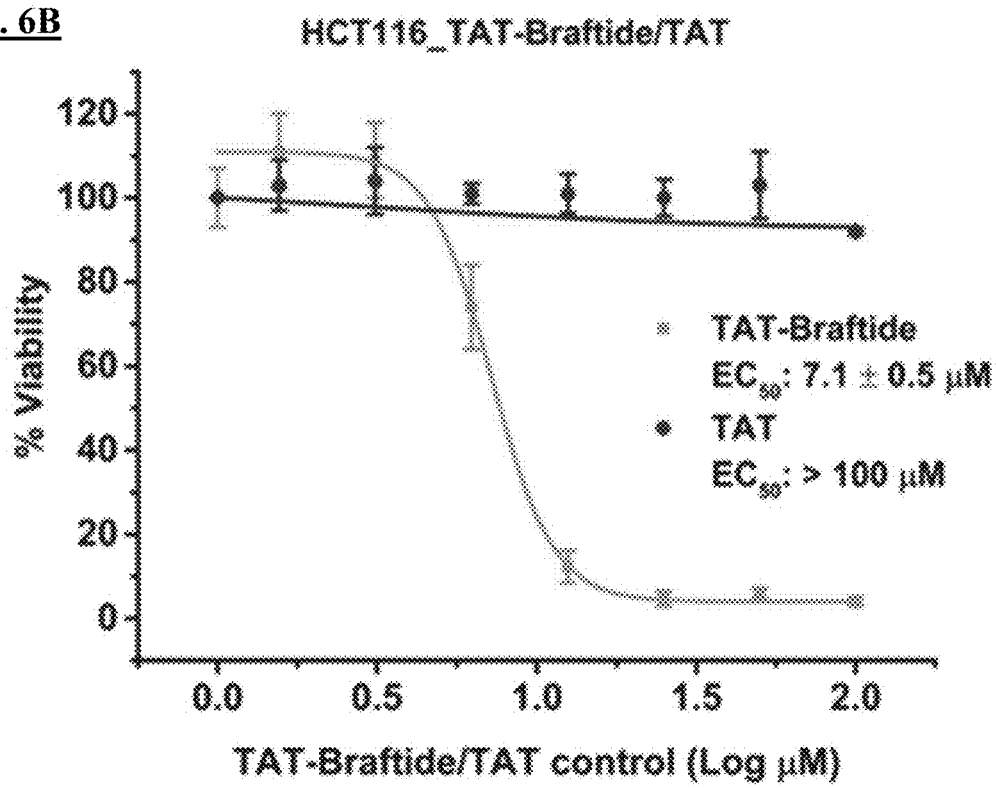
Figure 6C:
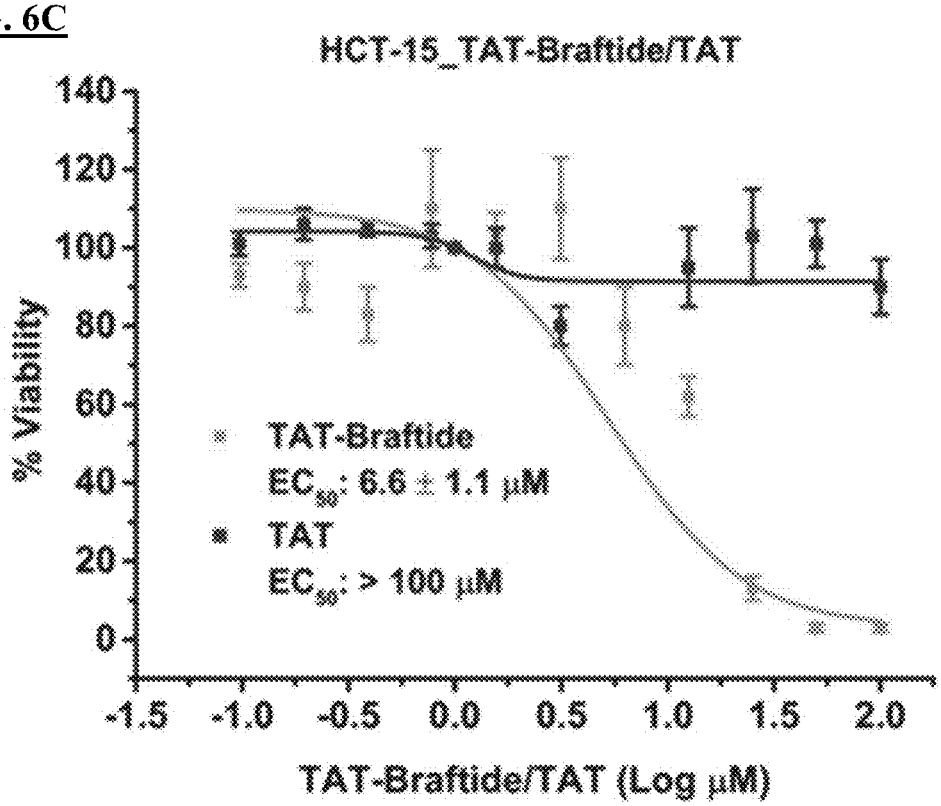

The dual mechanism of TAT-braftide inhibition on MAPK signaling was further explored in two cancer cell lines, HCT116 and HCT-15 (mutant KRAS G13D, colon carcinoma cell lines). Hyperactivated KRAS markedly increases the levels of RAS-dependent BRAF homodimers and BRAF/CRAF heterodimers. Cell-based assays with TAT-braftide illustrate inhibition of the MAPK pathway in the HCT116 cell line (FIG. 6A), as evidenced by diminished phospho-MEK and phospho-ERK, together with degradation of endogenous BRAF and MEK, with an IC$_{50}$ value below 10 μM. Without wishing to be limited by any theory, the discrepancy between the IC$_{50}$ values of braftide against HCT116 and HEK293 cells transiently transfected with FL-RAF is due to the protein level of RAF. The endogenous RAF protein level is at least 100-fold lower than that of overexpressed RAF in HEK293 cells. Since ATP-competitive BRAF inhibitors have been shown to cause tumor cell death primarily through apoptosis rather than necrosis, the apoptotic activity of TAT-braftide was evaluated on the two cancer cell lines via cell viability assays (FIGS. 6B and 6C). TAT-braftide treatment caused dose-dependent inhibition of cell growth of HCT116 and HCT-15 cells, with EC$_{50}$ values of 5.0 μM and 9.0 μM, respectively, demonstrating potent inhibitory activity on cell viability in RAS-mutated colon cancer cells. The TAT peptide was used as a negative control, and no cell death was observed at concentrations up to 100 μM (FIGS. 6B-6C).

Example 8

All RAF inhibitors developed to date belong to the ATP-competitive inhibitor. Structure-guided drug design led to the approval of vemurafenib and dabrafenib that preferentially stabilize the 'αCOUT' configuration. Unfortunately, they are ineffective against dimeric BRAF. 'αC-IN' inhibitors are designed to equally occupy both protomers of RAF dimers, therefore hold promise in dimeric BRAF-dependent tumors. However, paradoxical activation of MAPK signaling is a property of both 'αC-OUT' and 'αC-IN' inhibitors. Conversely, allosteric RAF inhibitors have been understudied.

Structures of BRAF have identified the key properties of the RAF dimer interface, which provides us a solid foundation to design dimer breakers through in silico approaches. The 10-mer braftide presented herein has demonstrated efficacy against BRAF$^{G469A}$ a representative of dimeric BRAF mutants. Braftide potently inhibits dimeric BRAF by eradicating both the catalytic and noncatalytic functions of BRAF. As a result, it successfully avoids negative cooperativity and paradoxical activation. This work further verifies that the RAF dimer interface is a drug target against malignancies driven by dimeric BRAF mutants or RAS mutants.

As shown herein, braftide treatment causes degradation of the MAPK complex. Further, this RAF degradation is mediated through the proteasome. These results uncover a previously unrecognized function of dimerization: sequestering RAF proteins in a conformation that is less prone to proteasome-mediated protein degradation. This finding has important implications. Targeted degradation of disease-causing proteins using proteolysis targeting chimeras (PROTACs) has emerged as a powerful strategy to combat cancer. Similar to PROTACs, braftide-triggered selective degradation of RAF and MEK could be advantageous over small molecule inhibitors. Other than inhibition of kinase activity, elimination of all functions of BRAF by protein degradation ensures a more complete inactivation of MAPK signaling. Moreover, the dual inhibition mechanism of braftide most likely circumvents reactivation of the same pathway and hence delays or prevents drug resistance by this mechanism, which is a common drawback of small molecule RAF inhibitors. ATP-competitive inhibitors are identified to promote RAF dimerization. This property can also enhance the half-life of RAF proteins, counteracting the efficacy of kinase inhibitors.

Structural analysis of various ATP-competitive RAF inhibitors suggest that the binding mode of an inhibitor can affect RAF dimerization. Inhibitors that binds to the kinase domain in the 'αCOUT' configuration disfavors dimer formation, suggesting that this feature can be utilized to dissociate enzyme inhibition from paradoxical activation. Since dimerization is necessary for activation of all three RAF kinases, braftide is expected to behave more or less like pan-RAF inhibitors. Several of this type of inhibitors are currently under clinical trials. One major concern for pan-RAF inhibitors is that toxicity might arise from blocking wild-type RAF proteins in healthy tissue. The kinase assays presented herein demonstrate that BRAF$^{G469A}$ is more prone to braftide inhibition.

Consistent with the notion that BRAF$^{V600E}$ can signal as a monomer, the effectiveness of braftide against BRAF$^{V600E}$ is dampened. Surprisingly, braftide inhibits ectopically expressed p61 BRAF$^{V600E}$, a spliced form of BRAF$^{V600E}$ that constitutively dimerizes in a RAS-independent manner. Its dimerization feature confers intrinsic resistance to BRAF inhibition in BRAF$^{V600E}$ melanoma patients, however the kinase activity of p61 BRAF$^{V600E}$ is not contingent on the dimer interface. Without wishing to be limited by any theory, in certain embodiments the observed inhibition effect of braftide stems from blocking the scaffolding function of p61 BRAF$^{V600E}$, rather than inhibiting the kinase activity of p61.

In summary, this work provides novel RAF inhibitors that evade negative cooperativity, paradoxical activation, and resistance mechanisms. Furthermore, such inhibitors are a valuable chemical probe to dissect the biological significance of RAF dimerization in MAPK signaling.

Enumerated Embodiments

The following exemplary embodiments are provided, the numbering of which is not to be construed as designating levels of importance.

Embodiment 1 provides a method of treating cancer in a subject, the method comprising administering to the subject a therapeutically effective amount of a polypeptide consisting essentially of sequence TRHVNILLFM (SEQ ID NO. 1).

Embodiment 2 provides the method of Embodiment 1, wherein the cancer comprises at least one oncogenic RAS mutation or BRAF mutation.

Embodiment 3 provides the method of any of Embodiments 1-2, wherein the cancer is selected from the group consisting of lung cancer, colorectal cancer, thyroid cancer, and melanoma.

Embodiment 4 provides the method of any of Embodiments 1-3, wherein the polypeptide is derivatized at one or more amino acid residues, wherein each derivatization independently comprises methylation, amidation, or acetylation.

Embodiment 5 provides the method of any of Embodiments 1-4, wherein the polypeptide is further fused to a cell penetrating peptide.

Embodiment 6 provides the method of Embodiment 5, wherein the cell penetrating peptide is any of SEQ ID NOs:2-40.

Embodiment 7 provides the method of any of Embodiments 5-6, wherein the cell penetrating peptide comprises TAT sequence GRKKRRQRRRPQ (SEQ ID NO:2).

Embodiment 8 provides the method of any of Embodiments 5-7, wherein the polypeptide is fused to the cell penetrating peptide via a linker.

Embodiment 9 provides the method of 9 Embodiment 8, wherein the linker comprises a polyethylene glycol (PEG) chain, a peptide, or a peptide nucleic acid (PNA).

Embodiment 10 provides the method of Embodiment 9, wherein the linker peptide comprises less than about 50 amino acids.

Embodiment 11 provides the method of any of Embodiments 1-10, wherein the polypeptide is cyclized.

Embodiment 12 provides the method of any of Embodiments 1-11, wherein the polypeptide allosterically inhibits kinase activity of BRAF dimer or blocks formation of BRAF dimer.

Embodiment 13 provides the method of Embodiment 12, wherein at least one of the following applies: the BRAF dimer is a BRAF homodimer, the BRAF dimer is BRAF/CRAF heterodimer, the BRAF dimer comprises BRAF V600E mutation, the BRAF dimer does not comprise BRAF V600E mutation, and the BRAF dimer comprises oncogenic BRAF G469A.

Embodiment 14 provides the method of any of Embodiments 1-13, wherein the administering of the polypeptide causes proteolysis of at least one of BRAF and MEK.

Embodiment 15 provides the method of any of Embodiments 1-14, wherein the administering of the polypeptide causes apoptosis in cancer cells.

Embodiment 16 provides the method of any of Embodiments 1-15, wherein the administering of the polypeptide causes no, or insignificant, apoptosis in non-cancerous cells.

Embodiment 17 provides the method of any of Embodiments 1-16, wherein the polypeptide is administered as part of a pharmaceutical composition.

Embodiment 18 provides the method of any of Embodiments 1-17, wherein the subject is not administered any additional chemotherapeutic agent or anti-cell proliferation agent.

Embodiment 19 provides the method of any of Embodiments 1-17, wherein the subject is not administered any additional chemotherapeutic agent or anti-cell proliferation agent in an amount sufficient to treat or prevent the cancer in the subject.

Embodiment 20 provides the method of any of Embodiments 1-19, further comprising administering to the subject at least one additional agent selected from the group consisting of radiation, a chemotherapeutic agent, an anti-cell proliferation agent, a gene therapy agent, and an immunotherapy agent.

Embodiment 21 provides the method of Embodiment 20, wherein the at least one additional agent is an ATP-competitive BRAF inhibitor.

Embodiment 22 provides the method of Embodiment 22, wherein the ATP-competitive BRAF inhibitor comprises dabrafenib or vemurafenib.

Embodiment 23 provides the method of any of Embodiments 1 20-22, wherein the polypeptide and at least one additional agent are coformulated or co-administered to the subject.

Embodiment 24 provides the method of any of Embodiments 1-23, wherein the subject is a mammal.

Embodiment 25 provides the method of any of Embodiments 1-24, wherein the subject is a human.

Embodiment 26 provides a polypeptide consisting essentially of the amino acid sequence TRHVNILLFM (SEQ ID NO. 1), wherein the polypeptide is at least one of the following: (i) derivatized at one or more amino acid residues, wherein each derivatization independently comprises methylation, amidation, or acetylation; (ii) fused to a cell penetrating peptide; (iii) cyclized.

Embodiment 27 provides the polypeptide of Embodiment 27, wherein the polypeptide is fused to the cell penetrating peptide via a linker comprising a polyethylene glycol (PEG) chain, a peptide, or a peptide nucleic acid (PNA).

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or ameliorating cancer in a subject, the method comprising administering to the subject a therapeutically effective amount of:
   a polypeptide consisting of amino acid sequence TRHVNILLFM (SEQ ID NO: 1),
   a polypeptide consisting of amino acid sequence TRHVNILLFM (SEQ ID NO: 1) linked to a cell penetrating peptide, or
   a polypeptide consisting of amino acid sequence TRHVNILLFM (SEQ ID NO: 1) which is linked through a linker to a cell penetrating peptide.

2. The method of claim 1, wherein the cancer comprises at least one oncogenic RAS mutation or BRAF mutation.

3. The method of claim 1, wherein the cancer is selected from the group consisting of lung cancer, colorectal cancer, thyroid cancer, and melanoma.

4. The method of claim 1, wherein the polypeptide is derivatized at one or more amino acid residues, wherein each derivatization independently comprises methylation, amidation, or acetylation.

5. The method of claim 1, wherein the cell penetrating peptide is any one of SEQ ID NOs:2-40.

6. The method of claim 1, wherein the cell penetrating peptide comprises TAT sequence GRKKRRQRRRPQ (SEQ ID NO:2).

7. The method of claim 1, wherein the polypeptide consists of amino acid sequence TRHVNILLFM (SEQ ID NO: 1) which is linked through a linker to a cell penetrating peptide.

8. The method of claim 7, wherein the linker comprises a polyethylene glycol (PEG) chain, a peptide, or a peptide nucleic acid (PNA).

9. The method of claim 8, wherein the linker peptide comprises less than about 50 amino acids.

10. The method of claim 1, wherein the polypeptide is cyclized.

11. The method of claim 1, wherein the polypeptide allosterically inhibits kinase activity of a BRAF dimer or blocks formation of a BRAF dimer.

12. The method of claim 11, wherein at least one of the following applies:
   the BRAF dimer is a BRAF homodimer,
   the BRAF dimer is a BRAF/CRAF heterodimer,
   the BRAF dimer comprises a $BRAF^{V600E}$ mutation,
   the BRAF dimer does not comprise a $BRAF^{V600E}$ mutation, and
   the BRAF dimer comprises an oncogenic $BRAF^{G469A}$ mutation.

13. The method of claim 1, wherein the administering of the polypeptide causes proteolysis of at least one of BRAF and MEK.

14. The method of claim 1, wherein the administering of the polypeptide causes apoptosis in cancer cells.

15. The method of claim 1, wherein the administering of the polypeptide causes no, or insignificant, apoptosis in non-cancerous cells.

16. The method of claim 1, wherein the polypeptide is administered as part of a pharmaceutical composition.

17. The method of claim 1, wherein the subject is not administered any additional chemotherapeutic agent or anti-cell proliferation agent.

18. The method of claim 1, wherein the subject is not administered any additional chemotherapeutic agent or anti-cell proliferation agent in an amount sufficient to treat or prevent the cancer in the subject.

19. The method of claim 1, further comprising administering to the subject at least one additional agent selected from the group consisting of radiation, a chemotherapeutic agent, an anti-cell proliferation agent, a gene therapy agent, and an immunotherapy agent.

20. The method of claim 19, wherein the at least one additional agent is an ATP-competitive BRAF inhibitor.

21. The method of claim 20, wherein the ATP-competitive BRAF inhibitor comprises dabrafenib or vemurafenib.

22. The method of claim 19, wherein the polypeptide and at least one additional agent are coformulated or co-administered to the subject.

\* \* \* \* \*

```
SEQUENCE LISTING

<160> NUMBER OF SEQ ID NOS: 51

<210> SEQ ID NO 1
<211> LENGTH: 10
<212> TYPE: PRT
<213> ORGANISM: Artificial Sequence
<220> FEATURE:
<223> OTHER INFORMATION: Chemically synthesized

<400> SEQUENCE: 1

Thr Arg His Val Asn Ile Leu Leu Phe Met
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Chemically synthesized

<400> SEQUENCE: 2

Gly Arg Lys Lys Arg Arg Gln Arg Arg Pro Gln
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Chemically synthesized

<400> SEQUENCE: 3

Gly Val Leu Arg Lys
1               5

<210> SEQ ID NO 4
<211> LENGTH: 4
<212> TYPE: PRT
<213> ORGANISM: Artificial Sequence
<220> FEATURE:
<223> OTHER INFORMATION: Chemically synthesized

<400> SEQUENCE: 4

Val Leu Arg Lys
1

<210> SEQ ID NO 5
<211> LENGTH: 3
<212> TYPE: PRT
<213> ORGANISM: Artificial Sequence
<220> FEATURE:
<223> OTHER INFORMATION: Chemically synthesized
```

```
<400> SEQUENCE: 5

Leu Arg Lys
1

<210> SEQ ID NO 6
<211> LENGTH: 4
<212> TYPE: PRT
<213> ORGANISM: Artificial Sequence
<220> FEATURE:
<223> OTHER INFORMATION: Chemically synthesized

<400> SEQUENCE: 6

Gly Tyr Ser Thr
1

<210> SEQ ID NO 7
<211> LENGTH: 3
<212> TYPE: PRT
<213> ORGANISM: Artificial Sequence
<220> FEATURE:
<223> OTHER INFORMATION: Chemically synthesized

<400> SEQUENCE: 7

Gly Tyr Ser
1

<210> SEQ ID NO 8
<211> LENGTH: 10
<212> TYPE: PRT
<213> ORGANISM: Artificial Sequence
<220> FEATURE:
<223> OTHER INFORMATION: Chemically synthesized

<400> SEQUENCE: 8

Arg Lys Thr Arg His Val Asn Ile Leu Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Chemically synthesized

<400> SEQUENCE: 9

Cys Arg Lys Thr Arg His Val Asn Ile Leu Leu Cys
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Chemically synthesized

<400> SEQUENCE: 10

Arg Gln Ile Lys Ile Trp Phe Gln Asn Arg Arg Met Lys Trp Lys Lys
1               5                   10                  15

<210> SEQ ID NO 11
<211> LENGTH: 10
<212> TYPE: PRT
<213> ORGANISM: Artificial Sequence
<220> FEATURE:
<223> OTHER INFORMATION: Chemically synthesized

<400> SEQUENCE: 11
```

```
Pro Arg Pro Leu Pro Phe Pro Arg Pro Gly
1               5                   10
```

<210> SEQ ID NO 12
<211> LENGTH: 19
<212> TYPE: PRT
<213> ORGANISM: Artificial Sequence
<220> FEATURE:
<223> OTHER INFORMATION: Chemically synthesized

<400> SEQUENCE: 12

```
Lys Met Thr Arg Ala Gln Arg Arg Ala Ala Ala Arg Arg Asn Arg Trp
1               5                   10                  15

Thr Ala Arg
```

<210> SEQ ID NO 13
<211> LENGTH: 21
<212> TYPE: PRT
<213> ORGANISM: Artificial Sequence
<220> FEATURE:
<223> OTHER INFORMATION: Chemically synthesized

<400> SEQUENCE: 13

```
Thr Arg Ser Ser Arg Ala Gly Leu Gln Phe Pro Val Gly Arg Val His
1               5                   10                  15

Arg Leu Leu Arg Lys
            20
```

<210> SEQ ID NO 14
<211> LENGTH: 20
<212> TYPE: PRT
<213> ORGANISM: Artificial Sequence
<220> FEATURE:
<223> OTHER INFORMATION: Chemically synthesized

<400> SEQUENCE: 14

```
Gly Leu Trp Arg Ala Leu Trp Arg Leu Leu Arg Ser Leu Trp Arg Leu
1               5                   10                  15

Leu Trp Arg Ala
            20
```

<210> SEQ ID NO 15
<211> LENGTH: 20
<212> TYPE: PRT
<213> ORGANISM: Artificial Sequence
<220> FEATURE:
<223> OTHER INFORMATION: Chemically synthesized

<400> SEQUENCE: 15

```
Lys Leu Arg Thr Arg Ala Gln Arg Arg Ala Ala Ala Arg Lys Asn Lys
1               5                   10                  15

Arg Asn Thr Arg
            20
```

<210> SEQ ID NO 16
<211> LENGTH: 29
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (1)..(9)
<223> OTHER INFORMATION: D-enantiomers

```
<400> SEQUENCE: 16

Arg Arg Arg Arg Arg Arg Arg Arg Lys Phe Val Arg Arg Ser Arg
1               5                   10                  15

Arg Pro Arg Thr Ala Ser Cys Ala Leu Ala Phe Val Asn
            20                  25

<210> SEQ ID NO 17
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (1)..(9)
<223> OTHER INFORMATION: D-enantiomers

<400> SEQUENCE: 17

Arg Arg Arg Gln Arg Arg Lys Lys Arg
1               5

<210> SEQ ID NO 18
<211> LENGTH: 15
<212> TYPE: PRT
<213> ORGANISM: Artificial Sequence
<220> FEATURE:
<223> OTHER INFORMATION: Chemically synthesized

<400> SEQUENCE: 18

Arg Arg Arg Arg Asn Arg Thr Arg Arg Asn Arg Arg Arg Val Arg
1               5                   10                  15

<210> SEQ ID NO 19
<211> LENGTH: 24
<212> TYPE: PRT
<213> ORGANISM: Artificial Sequence
<220> FEATURE:
<223> OTHER INFORMATION: Chemically synthesized

<400> SEQUENCE: 19

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 20
<211> LENGTH: 17
<212> TYPE: PRT
<213> ORGANISM: Artificial Sequence
<220> FEATURE:
<223> OTHER INFORMATION: Chemically synthesized

<400> SEQUENCE: 20

Thr Arg Gln Ala Arg Arg Asn Arg Arg Arg Arg Trp Arg Glu Arg Gln
1               5                   10                  15

Arg

<210> SEQ ID NO 21
<211> LENGTH: 12
<212> TYPE: PRT
<213> ORGANISM: Artificial Sequence
<220> FEATURE:
<223> OTHER INFORMATION: Chemically synthesized

<400> SEQUENCE: 21
```

```
Thr Ser Pro Leu Asn Ile His Asn Gly Gln Lys Leu
1               5                   10
```

<210> SEQ ID NO 22
<211> LENGTH: 13
<212> TYPE: PRT
<213> ORGANISM: Artificial Sequence
<220> FEATURE:
<223> OTHER INFORMATION: Chemically synthesized

<400> SEQUENCE: 22

```
Thr Arg Arg Gln Arg Thr Arg Arg Ala Arg Arg Asn Arg
1               5                   10
```

<210> SEQ ID NO 23
<211> LENGTH: 16
<212> TYPE: PRT
<213> ORGANISM: Artificial Sequence
<220> FEATURE:
<223> OTHER INFORMATION: Chemically synthesized

<400> SEQUENCE: 23

```
Ala Ala Val Ala Leu Leu Pro Ala Val Leu Leu Ala Leu Leu Ala Pro
1               5                   10                  15
```

<210> SEQ ID NO 24
<211> LENGTH: 10
<212> TYPE: PRT
<213> ORGANISM: Artificial Sequence
<220> FEATURE:
<223> OTHER INFORMATION: Chemically synthesized

<400> SEQUENCE: 24

```
Val Pro Met Leu Lys Pro Met Leu Lys Glu
1               5                   10
```

<210> SEQ ID NO 25
<211> LENGTH: 36
<212> TYPE: PRT
<213> ORGANISM: Artificial Sequence
<220> FEATURE:
<223> OTHER INFORMATION: Chemically synthesized

<400> SEQUENCE: 25

```
Lys Leu Ala Leu Lys Leu Ala Leu His Ala Leu Lys Ala Ala Leu Lys
1               5                   10                  15

Leu Ala Lys Leu Ala Leu Lys Leu Ala Leu Lys Ala Leu Lys Ala Ala
                20                  25                  30

Leu Lys Leu Ala
        35
```

<210> SEQ ID NO 26
<211> LENGTH: 27
<212> TYPE: PRT
<213> ORGANISM: Artificial Sequence
<220> FEATURE:
<223> OTHER INFORMATION: Chemically synthesized

<400> SEQUENCE: 26

```
Gly Ala Leu Phe Leu Ala Phe Leu Ala Ala Ala Leu Ser Leu Met Gly
1               5                   10                  15

Leu Trp Ser Gln Pro Lys Lys Lys Arg Arg Val
                20                  25
```

<210> SEQ ID NO 27

<211> LENGTH: 27
<212> TYPE: PRT
<213> ORGANISM: Artificial Sequence
<220> FEATURE:
<223> OTHER INFORMATION: Chmeically synthesized

<400> SEQUENCE: 27

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 28
<211> LENGTH: 17
<212> TYPE: PRT
<213> ORGANISM: Artificial Sequence
<220> FEATURE:
<223> OTHER INFORMATION: Chemically synthesized

<400> SEQUENCE: 28

Asn Ala Lys Thr Arg Arg His Glu Arg Arg Arg Lys Leu Ala Ile Glu
1               5                   10                  15

Arg

<210> SEQ ID NO 29
<211> LENGTH: 16
<212> TYPE: PRT
<213> ORGANISM: Artificial Sequence
<220> FEATURE:
<223> OTHER INFORMATION: Chemically synthesized

<400> SEQUENCE: 29

Arg Gln Ile Lys Ile Phe Phe Gln Asn Arg Arg Met Lys Phe Lys Lys
1               5                   10                  15

<210> SEQ ID NO 30
<211> LENGTH: 21
<212> TYPE: PRT
<213> ORGANISM: Artificial Sequence
<220> FEATURE:
<223> OTHER INFORMATION: Chemically synthesized

<400> SEQUENCE: 30

Lys Glu Thr Trp Trp Glu Thr Trp Trp Thr Glu Trp Ser Gln Pro Lys
1               5                   10                  15

Lys Lys Arg Arg Val
            20

<210> SEQ ID NO 31
<211> LENGTH: 15
<212> TYPE: PRT
<213> ORGANISM: Artificial Sequence
<220> FEATURE:
<223> OTHER INFORMATION: Chemically synthesized

<400> SEQUENCE: 31

Ser Asp Leu Trp Glu Met Met Met Val Ser Leu Ala Cys Gln Tyr
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Chemically synthesized

```
<400> SEQUENCE: 32

Arg Val Ile Arg Val Trp Phe Gln Asn Lys Arg Cys Lys Asp Lys Lys
1               5                   10                  15

<210> SEQ ID NO 33
<211> LENGTH: 18
<212> TYPE: PRT
<213> ORGANISM: Artificial Sequence
<220> FEATURE:
<223> OTHER INFORMATION: Chemically synthesized

<400> SEQUENCE: 33

Leu Leu Ile Ile Leu Arg Arg Arg Ile Arg Lys Gln Ala His Ala His
1               5                   10                  15

Ser Lys

<210> SEQ ID NO 34
<211> LENGTH: 8
<212> TYPE: PRT
<213> ORGANISM: Artificial Sequence
<220> FEATURE:
<223> OTHER INFORMATION: Chemically synthesized

<400> SEQUENCE: 34

Arg Arg Arg Arg Arg Arg Arg Trp
1               5

<210> SEQ ID NO 35
<211> LENGTH: 41
<212> TYPE: PRT
<213> ORGANISM: Artificial Sequence
<220> FEATURE:
<223> OTHER INFORMATION: Chemically synthesized

<400> SEQUENCE: 35

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Arg Arg Arg Arg Arg Arg Arg Arg Arg
        35                  40

<210> SEQ ID NO 36
<211> LENGTH: 18
<212> TYPE: PRT
<213> ORGANISM: Artificial Sequence
<220> FEATURE:
<223> OTHER INFORMATION: Chemically synthesized

<400> SEQUENCE: 36

Val Arg Leu Pro Pro Pro Val Arg Leu Pro Pro Pro Val Arg Leu Pro
1               5                   10                  15

Pro Pro

<210> SEQ ID NO 37
<211> LENGTH: 13
<212> TYPE: PRT
<213> ORGANISM: Artificial Sequence
<220> FEATURE:
<223> OTHER INFORMATION: Chemically synthesized

<400> SEQUENCE: 37

Cys Gly Gly Gly Pro Lys Lys Lys Arg Lys Val Glu Asp
1               5                   10
```

<210> SEQ ID NO 38
<211> LENGTH: 18
<212> TYPE: PRT
<213> ORGANISM: Artificial Sequence
<220> FEATURE:
<223> OTHER INFORMATION: Chemically synthesized

<400> SEQUENCE: 38

Arg Gly Gly Arg Leu Ser Tyr Ser Arg Arg Phe Ser Thr Ser Thr
1               5                   10                  15

Gly Arg

<210> SEQ ID NO 39
<211> LENGTH: 11
<212> TYPE: PRT
<213> ORGANISM: Artificial Sequence
<220> FEATURE:
<223> OTHER INFORMATION: Chemically synthesized

<400> SEQUENCE: 39

Tyr Gly Arg Lys Lys Arg Arg Gln Arg Arg
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Chemically synthesized

<400> SEQUENCE: 40

Gly Arg Lys Lys Arg Arg Gln Arg Arg Arg Pro Pro Gln Gln
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Chemically synthesized

<400> SEQUENCE: 41

Arg Lys Lys Arg Arg Gln Arg Arg
1               5

<210> SEQ ID NO 42
<211> LENGTH: 13
<212> TYPE: PRT
<213> ORGANISM: Artificial Sequence
<220> FEATURE:
<223> OTHER INFORMATION: Chemically synthesized

<400> SEQUENCE: 42

Gly Arg Arg Arg Arg Arg Arg Arg Arg Pro Pro Gln
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Chemically synthesized

<400> SEQUENCE: 43

Gly Arg Lys Lys Arg Arg Gln Arg Arg Arg Pro Trp Gln

<210> SEQ ID NO 44
<211> LENGTH: 27
<212> TYPE: PRT
<213> ORGANISM: Artificial Sequence
<220> FEATURE:
<223> OTHER INFORMATION: Chemically synthesized

<400> SEQUENCE: 44

Gly Trp Thr Leu Asn Ser Ala Gly Tyr Leu Leu Gly Lys Ile Asn Leu
1               5                   10                  15
Lys Ala Leu Ala Ala Leu Ala Lys Lys Ile Leu
            20                  25

<210> SEQ ID NO 45
<211> LENGTH: 34
<212> TYPE: PRT
<213> ORGANISM: Artificial Sequence
<220> FEATURE:
<223> OTHER INFORMATION: Chemically synthesized

<400> SEQUENCE: 45

Asp Ala Ala Thr Ala Thr Arg Gly Arg Ser Ala Ala Ser Arg Pro Thr
1               5                   10                  15
Glu Arg Pro Arg Ala Pro Ala Arg Ser Ala Ser Arg Pro Arg Arg Pro
            20                  25                  30
Val Asp

<210> SEQ ID NO 46
<211> LENGTH: 16
<212> TYPE: PRT
<213> ORGANISM: Artificial Sequence
<220> FEATURE:
<223> OTHER INFORMATION: Chemically synthesized

<400> SEQUENCE: 46

Arg Gln Ile Lys Ile Trp Phe Gln Asn Arg Arg Met Lys Trp Lys Lys
1               5                   10                  15

<210> SEQ ID NO 47
<211> LENGTH: 9
<212> TYPE: PRT
<213> ORGANISM: Artificial Sequence
<220> FEATURE:
<223> OTHER INFORMATION: Chemically synthesized

<400> SEQUENCE: 47

Arg Arg Arg Arg Arg Arg Arg Arg Arg
1               5

<210> SEQ ID NO 48
<211> LENGTH: 10
<212> TYPE: PRT
<213> ORGANISM: Artificial Sequence
<220> FEATURE:
<223> OTHER INFORMATION: Chemically synthesized

<400> SEQUENCE: 48

Thr His His Val Asn Ile Leu Leu Phe Met
1               5                   10

<210> SEQ ID NO 49
<211> LENGTH: 18
<212> TYPE: PRT

```
<213> ORGANISM: Artificial Sequence
<220> FEATURE:
<223> OTHER INFORMATION: Chemically synthesized

<400> SEQUENCE: 49

Gly Val Leu Arg Lys Thr Arg His Val Asn Ile Leu Leu Phe Met Gly
1               5                   10                  15

Tyr Ser

<210> SEQ ID NO 50
<211> LENGTH: 18
<212> TYPE: PRT
<213> ORGANISM: Artificial Sequence
<220> FEATURE:
<223> OTHER INFORMATION: Chemically synthesized

<400> SEQUENCE: 50

Ala Val Leu Arg Lys Thr Arg His Val Asn Ile Leu Leu Phe Met Gly
1               5                   10                  15

Tyr Met

<210> SEQ ID NO 51
<211> LENGTH: 18
<212> TYPE: PRT
<213> ORGANISM: Artificial Sequence
<220> FEATURE:
<223> OTHER INFORMATION: Chemically synthesized

<400> SEQUENCE: 51

Gln Val Leu Arg Lys Thr Arg His Val Asn Ile Leu Leu Phe Met Gly
1               5                   10                  15

Phe Met
```